(12) United States Patent
Labrie

(10) Patent No.: US 6,964,955 B2
(45) Date of Patent: Nov. 15, 2005

(54) PHARMACEUTICAL COMPOSITIONS AND USES FOR ANDROST-5-ENE-3β, 17β-DIOL

(75) Inventor: Fernand Labrie, Sainte-foy (CA)

(73) Assignee: Endorecherche, Inc. (CA)

(*) Notice: Subject to any disclaimer, the term of this patent is extended or adjusted under 35 U.S.C. 154(b) by 33 days.

(21) Appl. No.: 10/166,463

(22) Filed: Jun. 10, 2002

(65) Prior Publication Data
US 2002/0187965 A1 Dec. 12, 2002

Related U.S. Application Data

(60) Division of application No. 09/332,356, filed on Jun. 11, 1999, now Pat. No. 6,432,940, which is a continuation-in-part of application No. 09/096,286, filed on Jun. 11, 1998, now abandoned.

(51) Int. Cl.$^7$ .............................................. A61K 31/56
(52) U.S. Cl. ..................................................... 514/179
(58) Field of Search ........................................ 514/179

(56) References Cited

U.S. PATENT DOCUMENTS

| | | |
|---|---|---|
| 3,742,951 A | 7/1973 | Zaffaroni |
| 3,797,444 A | 3/1974 | Stubbs |
| 4,064,654 A | 12/1977 | Olson |
| 4,162,037 A | 7/1979 | Koyama |
| 4,568,343 A | 2/1986 | Leeper et al. |
| 4,624,665 A | 11/1986 | Nuwayser |
| 4,634,694 A | 1/1987 | Loozen et al. ............... 514/177 |
| 4,666,441 A | 5/1987 | Andriola |
| 5,071,644 A | 12/1991 | Viegas et al. |
| 5,071,657 A | 12/1991 | Oloff et al. |
| 5,135,480 A | 8/1992 | Bannon et al. |
| 5,154,922 A | 10/1992 | Govil et al. |
| 5,206,008 A | 4/1993 | Loria |
| 5,387,583 A | 2/1995 | Loria |
| 5,461,042 A | 10/1995 | Loria |
| 5,641,768 A | 6/1997 | Loria .......................... 514/182 |
| 5,728,688 A | 3/1998 | Labrie |
| 5,798,347 A | 8/1998 | Labrie |
| 5,807,849 A | 9/1998 | Labrie |
| 5,837,700 A | 11/1998 | Labrie |
| 5,843,932 A | 12/1998 | Labrie |
| 5,872,114 A | 2/1999 | Labrie |
| 5,877,216 A * | 3/1999 | Place et al. .................. 514/573 |
| 5,922,700 A | 7/1999 | Labrie |
| 6,284,262 B1 * | 9/2001 | Place ........................... 424/435 |
| 6,294,550 B1 * | 9/2001 | Place et al. .................. 514/302 |
| 6,306,841 B1 * | 10/2001 | Place et al. .................. 514/149 |

FOREIGN PATENT DOCUMENTS

| | | |
|---|---|---|
| EP | 0279982 | 11/1987 |
| EP | 0424954 | 5/1991 |
| FR | 816689 | 7/1961 |
| GB | 2185187 | 6/1986 |
| JP | 03-209328 | 9/1991 |
| JP | 8-505629 | 6/1996 |
| JP | 3361523 | 10/2002 |
| WO | 9316704 | 9/1993 |
| WO | WO 93/20696 | 10/1993 |
| WO | 9416709 | 8/1994 |
| WO | 9703676 | 2/1997 |
| WO | 9856386 | 12/1998 |
| WO | 99/63973 | * 12/1999 |

OTHER PUBLICATIONS

Scanning Electron Microscopy, vol. II, issued 1978, (USA), Lamb et al., "Modulation of the female mouse genial treact by hormones", pp. 773–778.*

Hackenberg, R., et al., "Estrogen and androgen receptor mediated stimulation and inhibition of proliferation by androst–5–ene–3beta, 17 beta–diol in human mammary in cancer cells", *J. Steroid Biochem Mol Biol*, Nov. 1993; 46(5): 597–603.

Boccuzzi G., et al., "5–ene–androsterone–3beta, 17beta–diol inhibits the growth of MCF–7 breast cancer cells when estrogen receptors are blocked by estradiol", *Br J Cancer*, Dec. 1994; 70(6):1035–9.

Boccuzzi G., et al., "Influence of dehydroepiandrosterone and 5–ene–androsterone–3beta, 17beta–diol on the growth of MCF–7 human breast cancer cells induced by 17beta–estradiol" *Anticancer Res*, May–Jun. 1992; 12(3):799–803.

Printout list of patent family for U.S. Patent 4,634,694 (Hungarian Patent No. 192286B).

Bird, et al., Acta Endo., 99(2):309–313 (1982).
Dauvois, et al., Breast Cancer Res., 13(1):61–69 (1989).
Tournaire, CAH. Med., 15(9):583–588 (1974).
Araneo, et al., J. Surg. Res., 59(2):250–262 (1995).
Kuiper, et al., Frontiers In ndo., 19(4):253–286 (1998).
Dorgan, et al., Cancer Epid., Biomarkers and Prev., 6(3):177–81 (1997).
Yoshimoto, et al., Horumon to Rinsho, Clin. Endo., 31(8):815–22 (1983).
Simard, et al., J. Steroid Biochem., 26(5):539–546 (1987).
Drugu 49784 Dunn, et al., abstract (1996).
Embase AN 95163258, Krause, abstract (1995).
Dunn, et al., Arch. Derm., 133(3):339–42, abstract (1996).
Couillard, et al., Maturitas, 27:80 (1997).
Luo, et al., Endocrinology, 138(10):4435–4444 (1997).
Pasqualini, J. Steroid Biochem. and Molecular Biology, 45(1–3):167–172 (1993).
Boccuzzi, et al., Anticancer Res., 13(6a):2267–2272 (1993).
Dowsett, et al., J. Clinical Endo. and Metab., 66(4):672–677 (1988).

(Continued)

Primary Examiner—Kevin E. Weddington
(74) Attorney, Agent, or Firm—Ostrolenk, Faber, Gerb & Soffen, LLP

(57) ABSTRACT

Androst-5-ene-3β,17βdiol is used to treat or reduce the likelihood of acquiring osteoporosis or menopausal symptoms, or other diseases affected by estrogen receptor activity, and for conditions which respond well to DHEA treatment, but where a higher ratio of estrogenic to androgenic effects is desired. Combination therapies are included, as are kits and pharmaceutical compositions for providing the active ingredients of claimed methods and combinations.

2 Claims, 18 Drawing Sheets

OTHER PUBLICATIONS

Meyskens, Cancer Invest., 6(5):609–614 (1988).
Kreitmann & Bayard, J. Steroid Biochem., 11:1589–1595 (1979).
Adams, et al., Cancer Res., 41:4720–4926 (1981).
Belanger, et al., Ann. NY Acad. Sci., 586:93–100 (1990).
Furlanetto, et al., J. Clin. Invest., 60:648 (1977).
Korenman, "Sexual Dysfunctions", Williams Textbook of Endo., pp. 1033–1048 (1992).
Nestler, et al., J. Clin. Endo. Metab., 66:57–61 (1988).
Masters, et al., J. Natl. Cancer Inst., 58:1263–1265 (1977).
Anderson, et al., Brit. J. Cancer, 46:376–382 (1982).
Potten, et al., Brit J. Cancer, 58:163–170 (1988).
Going, et al., Am. J. Pathol., 130:193–204 (1988).
Ferland, et al., Hypothalamus and Endocrine Functions, pp. 191–209 (1976).
Romieu, et al., Cancer, 66:2253–2263 (1990).
Koller, et al., STP Pharma 3(2):115–124 (1987).
Belanger, et al., Clinical and Invest. Med., 11(5):321–326 (1988).
Pelletier, et al., J. Mol. Endocr., 1:213–223 (1988).
Rodbard, et al., Karolinska Symposia, Steroid Assay by Protein binding, Mar. 23–25, 1970.
Poulin and Labrie, Cancer Res., 46:4933–4937 (1986).
Tindall, Walter J., Preparations for cosmetic and therapeutic treatment of the skin, NL 88000180 May 16, 1958 (copy of abstract).
Herbert J. Buschbaum, The Menopause, Springer–Verlag, New York, (1983) pp. 22–23 and pp. 73–84.
Abstract: Luo, et al., Effects of Combination of Dehydroepian–Drosterone and EM–800 on Bone Mass, Serum Lipids, and The Development of Dimethylbenz (A) Anthracene (DMBA)–Induced Mammary Carcinoma in the Rat, Breast Cancer Research & Treatment (1997) (vol. 46, No. 1).

Steve Couillard, et al., Effect of Dehydroepiandrosterone and The Antiestrogen EM–800 on Growth of Human ZR–75–1 Breast Cancer Xenografts, Jou. of the Natl. Cancer Inst. (1998) vol. 90, No. 10.
Hungarian Novelty Search Report of Application No. P01 02483 dated Oct. 14, 2002.
M. Shiraki, et al.: "The effect of estrogen and sex steroids and thyroid hormone preparation on bone mineral density in senile osteoporosis—a comparative study of the effect of 1 alpha–hydroxycholecalciferol (1 alpha–OHD3) on senile osteoporosis", MEDLINE abstract of Nippon Naibunpi Gakkai Zasshi, vol. 67, No. 2, pp. 84–95, Feb. 20, 1991.
Fernand Labrie, et al.: "Interactions between Estrogens, Androgens, Progestins, and Glucocorticoids in ZR–75–1 Human Breast Cancer Cells", *Annals of the New York Academy of Sciences*, New York Academy of Sciences, New York, NY, 199, vol. 585, pp. 130–148, XP–000852949.
Japanese Office Action dated Apr. 9, 2004 and translation.
Hackenberg, R., et al., "Estrogen and androgen receptor mediated stimulation and inhibition of proliferation by androst–5–ene–3beta, 17 beta–diol in human mammary in cancer cells", *J. Steroid Biochem Mol Biol*, Nov. 1993; 46(5):597–603.
Boccuzzi G., et al., "5–ene–androsterone–3beta–17beta–diol inhibits the growth of MCF-7 breast cancer cells when estrogen receptors are blocked by estradiol", *Br J Cancer*, Dec. 1994;70(6):1035–9.
Boccuzzi G., et al., "Influence of dehydroepiandrosterone and 5–ene–androsterone–3beta, 17beta–diol on the growth of MCF–7 human breast cancer cells induced by 17beta–estradiol"*Anticancer Res*, May–Jun 1992; 12(3):799–803.

* cited by examiner

PHARMACEUTICAL COMPOSITIONS AND USES FOR ANDROST-5-ENE-3β, 17β-DIOL

CROSS REFERENCE TO RELATED APPLICATIONS

This is a divisional of U.S. patent application Ser. No. 09/332,356, filed Jun. 11, 1999 now U.S. Pat. No. 6,432,940, in the amount of Fernand LABRIE and entitled "PHARMACEUTICAL COMPOSITIONS AND USES FOR ANDROST-5-ENE-3BETA, 17BETA-DIOL", which is a continuation-in-part application U.S. patent application Ser. No. 09/096,286, filed Jun. 11, 1998, now abandoned, in the name of Fernand LABRIE and also entitled "PHARMACEUTICAL COMPOSITIONS AND USES FOR ANDROST-5-ENE-3BETA, 17BETA-DIOL".

BACKGROUND OF THE INVENTION

1. Field of the Invention

The present invention relates to pharmaceutical compositions, kits and methods for preventing and treating reduced or imbalanced concentrations of sex steroids and conditions which can respond favorably to increased activity of androgens and/or estrogens. The invention utilizes androst-5-ene-3β, 17β-diol (hereinafter 5-DIOL) or compounds converted in vivo to 5-DIOL 2. Description of the Related Art 5-DIOL is a compound biosynthesized from DHEA through the action of reductive 17β-hydroxysteroid dehydrogenase (17β-HSD) and is a weak estrogen. It has an 85-fold lower affinity than 17β-estradiol ($E_2$) for the estrogen receptor in rat anterior pituitary gland cytosol (Simard and Labrie, J. Steroid Biochem., 26: 539–546, 1987), further confirming the data obtained on the same parameter in human myometrial and breast cancer tissue (Kreitmann and Bayard, J. Steroid Biochem., 11: 1589–1595, 1979; Adams et al., Cancer Res., 41: 4720–4926, 1981; Poulin and Labrie, Cancer Res., 46: 4933–4937, 1986).

At concentrations well within the range of the plasma levels found in adult women, 5-DIOL enhances cell proliferation and progesterone receptor levels in human mammary tumor ZR-75-1 cells which lack 3β-hydroxysteroid dehydrogenase/D5-D4 isomerase activity (Poulin and Labrie, Cancer Res., 46: 4933–4937, 1986) and increases the estrogen-dependent synthesis of the 52 kDa glycoprotein in MCF-7 cells (Adams et al., Cancer Res., 41: 4720–4926, 1981).

In general, it is known that the serum levels of DHEA and DHEA-S decrease with age and correspondingly, that there is a dramatic reduction in the formation of androgens and estrogens in peripheral target tissues and a marked decrease in the biochemical and cellular functions induced by sex steroids. As a result, DHEA and DHEA-S have been used in the treatment of a variety of conditions which are associated with decrease and/or imbalances in the levels of sex steroids. Recently, we have found that the serum levels of 5-diol decrease markedly with age.

Osteoporosis, a condition which affects both men and women, is associated with a decrease in androgens and estrogens. Estrogens have been shown to decrease the rate of bone degradation while androgens have been shown to build bone mass.

Menopausal symptoms have also been associated with a loss of estrogens, and low dose estrogen therapy is commonly used in perimenopausal and menopausal women to relieve vasomotor symptoms, urogenital atrophy, irritability, sleep problems, loss of energy, osteoporosis, and other symptoms associated with menopause.

In addition, breast cancer, cardiovascular disease, and insulin resistance have been associated with decreased serum levels of DHEA and DHEA-S and both DHEA and DHEA-S have been suggested to prevent or treat these conditions. DHEA has also been suggested to have beneficial effects in the treatment and/or prevention of obesity, diabetes, atherosclerosis, chemically-induced breast, skin, and colon cancer, autoimmune diseases, Alzheimer's disease, loss of memory, aging and to support energy, muscle mass, and longevity. Uses of DHEA as well as the benefits of androgen and estrogen therapy are discussed in International Patent Publication WO 94/16709.

DHEA and DHEA-S have been suggested to be better for the treatment of these conditions than standard estrogen and androgen therapy since the action of DHEA and DHEA-S is targeted to the tissue which can convert DHEA and/or DHEA-S to specific sex steroids. However, high doses of DHEA are required to get the necessary estrogen and androgenic effects. Most importantly, the androgenic effects of DHEA are predominant and therefore, for conditions in which a higher proportion of estrogens is desired or where androgenic side effects are a problem, especially in women, the present invention permits a better proportion of estrogenic versus androgenic effects.

SUMMARY OF THE INVENTION

It is an object of the present invention to provide pharmaceutical compositions and kits which include 5-DIOL or prodrugs converted thereto in vivo. In some embodiments, the pharmaceutical compositions consist essential of 5-DIOL.

It is also an object of the present invention to provide methods of treating and preventing imbalances or reductions in the levels of sex steroid hormones (androgens and/or estrogens) raising 5-DIOL levels in a patient in need of such treatment or prevention.

It is a further object of this invention to provide methods of or treating or reducing the risk of onset of conditions which respond favorably to estrogenic activity, including vaginal atrophy, hypogonadism, diminished libido, skin atrophy, urinary incontinence, lipid, and lipoprotein imbalance, atherosclerosis, cardiovascular disease and symptoms of menopause (hot flushes, sleep disorders, Alzheimer's disease, Parkinson's disease, mental disorders, depression, loss of memory) by administering 5-DIOL. It is a further object of this invention to provide methods of preventing or treating conditions which respond favorably to androgenic activity, including breast cancer, ovarian cancer, endometrial cancer, diminished libido, skin atrophy, skin dryness, osteoporosis and symptoms of menopause by administering 5-DIOL. A number of diseases that are affected by sex steroids (e.g. osteoporosis) respond favorably to both androgens and estrogens.

A patient in need of treatment or reducing the risk of onset of a given disease is one who has either been diagnosed with such disease or one who is susceptible to acquiring such disease.

Except where otherwise noted or where apparent from context, dosages herein refer to weight of active compounds unaffected by pharmaceutical excipients, diluents, carries or other ingredients, although such additional ingredients are desirably included, as shown in the examples herein. Any dosage form (capsule, tablet, injection or the like) commonly used in the pharmaceutical industry is appropriate for use herein, and the terms "excipient," "diluent" or "carrier" include such non-active ingredients as are typically included, together with active ingredients in such dosage forms in the industry. For example, typical capsules, pills, enteric coatings, solid or liquid diluents or excipients, flavorants, preservatives, or the like are included.

The invention also includes use of an active agent in the manufacture of a medicament for treatment of a disease specified herein as susceptible to that agent, or one component of a combination in the manufacture of a medicament for treatment of a disease, where the treatment further includes another component of the claimed combination therapy.

It is an additional object of this invention to provide novel contraceptive methods which include administering 5-DIOL.

5-DIOL is a metabolite of dehydroepiandrosterone (DHEA). It has now been discovered that 5-DIOL has an unexpected variation (relative to DHEA) in its androgenic and estrogenic effects. In particular, 5-DIOL is five-fold more estrogenic than DHEA while its androgenic activity is only one- to two-fold higher than that of DHEA, thus giving the estrogenic to androgenic ratio of approximately 3.0 for 5-DIOL compared with DHEA. On the other hand, at higher doses, 5-DIOL produces maximal effects less androgenic than DHEA. Thus, the relative estrogenic versus androgenic effects of administering 5-DIOL lie more toward estrogenic effect than does a corresponding dosage of DHEA. Therefore, 5-DIOL is particularly useful in treating and preventing conditions involving low levels of sex steroids where the estrogen level, in particular, has fallen (i.e. more so than the androgen level). Indeed the invention is useful wherever an estrogenic effect is desired to a greater extent than is an androgenic effect. As explained below, 5-DIOL may be administered alone or in combination with other therapeutic agents such as antiestrogens, androgens, progestins, estrogens, DHEA, DHEA-sulfate, LHRH agonists or antagonists, inhibitors of 17β-hydroxysteroid dehydrogenase, aromatase inhibitors, inhibitors of gonadal sex steroid secretion, as part of a combination therapy.

In the context of the invention, any prodrugs of 5-DIOL may be used in place of 5-DIOL, including 5-DIOL-fatty acids, as these will also increase the serum levels of 5-DIOL.

Other features and advantages of the present invention will become apparent from the following description of the invention which refers to the accompanying drawings.

| EM-760 | dehydroepiandrosterone |
|---|---|
| EM-900 | androst-5-ene-3β,17β-diol |
| EM-1304 | androst-5-ene-3β,17β-diol 3-acetate |
| EM-1305-CS | androst-5-ene-3β,17β-diol diacetate |
| EM-1397 | androst-5-ene-3β,17β-diol acetate 17 benzoate |
| EM-1400 | androst-5-ene-3β,17β-diol dibenzoate |
| EM-1410 | androst-5-ene-3β,17β-diol dipropionate |
| EM-1474-D | androst-5-ene-3β,17β-diol dihemisuccinate |

Figure 18:
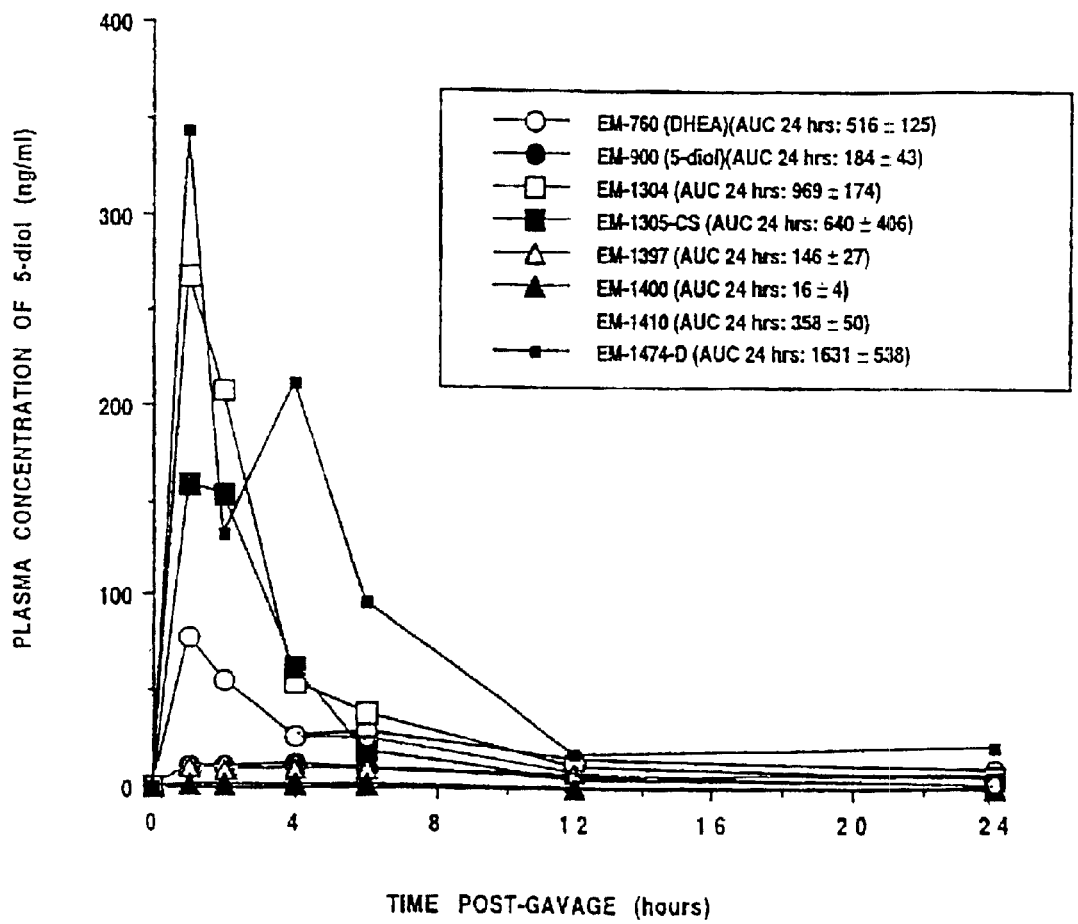

FIG. 18 shows the plasma concentration of androst-5-ene-3β,17β-diol (ng/mL) (Y axis) in function of time (X-axis) after a single oral absorption of prodrugs of androst-5-ene-3β,17β-diol (150 μmol/rat) in male rats. In the box, AUC 25h of androst-5-ene-3β,17β-diol induced by these compounds is reported.

| EM-760 | dehydroepiandrosterone |
|---|---|
| EM-900 | androst-5-ene-3β,17β-diol |
| EM-1304 | androst-5-ene-3β,17β-diol 3-acetate |
| EM-1305-CS | androst-5-ene-3β,17β-diol diacetate |
| EM-1397 | androst-5-ene-3β,17β-diol acetate 17 benzoate |
| EM-1400 | androst-5-ene-3β,17β-diol dibenzoate |
| EM-1410 | androst-5-ene-3β,17β-diol dipropionate |
| EM-1474-D | androst-5-ene-3β,17β-diol dihemisuccinate |

In Vivo Assays of Bioavailability of the prodrugs of androst-5-ene-3β,17β-diol

1) Principle

The assays of the bioavailability of prodrugs of androst-5-ene-3β,17β-diol were performed in male Sprague Dawley rats by measuring the plasma concentrations of the compounds after single oral administration of the compounds.

2) Animals and treatment

Male Sprague-Dawley rats [Crl:CD(SB)Br] weighing 275–350 g were obtained from Charles-River Canada Inc. and housed 2 per cage during the acclamation period and individually during the study period. The animals were maintained under a regimen of 12 hours light; 12 hours dark (lights on at 08:00). Animals received certified Rodent feed (Lab Diet #5002, pellets) and tap water ad libitum. Rats were fasted (access to water only) starting on the evening prior to dosing.

Each compound to be tested was administered to three animals as a suspension in 0.4% methylcellulose by oral gavage at a dose of 150 μmol/rat. One blood sample of –0.7 ml was collected from the jugular vein of rats under Isoflurane-induced anesthesia at 1, 2, 3, 4 and 7 hours post-gavage. Blood samples were immediately transferred into a refrigerated 0.75 ml Microtainer containing EDTA and kept in an ice-water bath until centrifugation at 3000 rpm for 10 minutes. Plasma separation was performed rapidly (less than 50 minutes) after blood collection). One aliquot of 0.25 ml of plasma was then transferred into a borosilicate tube (3×100) and was rapidy frozen on dry-ice. Plasma samples were kept at –80° C. until measurement of plasma concentration of the sex steroid or sex steroid precursors by GC-MS.

DETAILED DESCRIPTION OF THE INVENTION

It is believed that 5-DIOL may be used, in accordance with the invention, for the treatment of any disease known to respond favorably to treatment with DHEA with the added benefits related to its more favorable ratio of estrogenic versus androgenic activities and its lower maximal androgenic activity relative to DHEA. Administering 5-DIOL directly in accordance with the invention, has a number of advantages over administering DHEA, as discussed herein.

Applicant has discovered that 5-DIOL produces significantly different androgenic and estrogenic effects than does DHEA. In particular, 5-DIOL is shown to produce less potential androgenic or masculinizing effects for a given production of estrogenic effects than does DHEA. Therefore, 5-DIOL is particularly beneficial in treating conditions which require estrogenic activity with minimal androgenic activity. In fact, after menopause, women have a deficit of both androgens and estrogens although the ratio of estrogen/androgen is lower than before menopause. Women thus require a more favorable estrogen-androgenic ratio to compensate the loss of estradiol secretion by the ovaries. DHEA cannot compensate for this ovarian estrogenic deficit but will only replace the lowered secretion of DHEA-S and DHEA by the andrenals.

In particular, the production of the active androgen DHT and its precursor 4-dione by administering DHEA ranged, for increasing dosages, from 30 to 125% greater than obtained with 5-DIOL administration. On the other hand, a 53% greater production of testosterone was obtained with DHEA than by administering 5-DIOL. 4-dione is a steroid which is itself a weak androgen but is particularly efficiently transformed intracellularly into the more potent androgens testosterone, and DHT. The data shows that the maximum level of serum DHT reached after 5-DIOL was less than half of the maximum level reached with DHEA, and that at a relatively low dosage levels, the androgenic effect of 5-DIOL reaches a plateau of maximum activity much lower than that achieved by DHEA.

Figure 10:
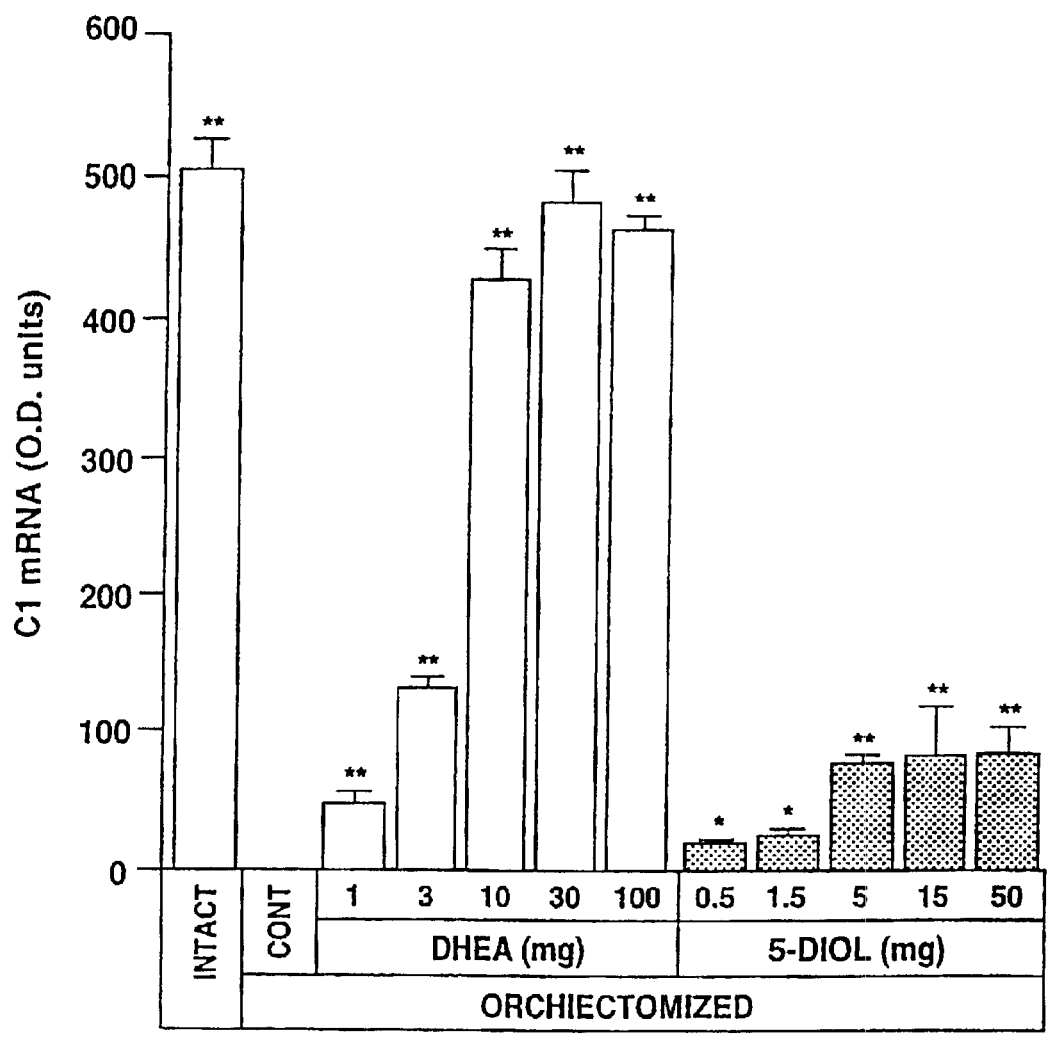
FIG. 10 is a graph of the effect of increasing doses of DHEA or 5-DIOL, administered percutaneously twice daily for 7 days, on the concentration of the mRNA encoding the Cl component of prostatic binding protein (PBP-Cl) in the ventral prostate of orchiectomized rats, a measure of androgenic effect. Intact animals are used as additional controls.
Figure 11:
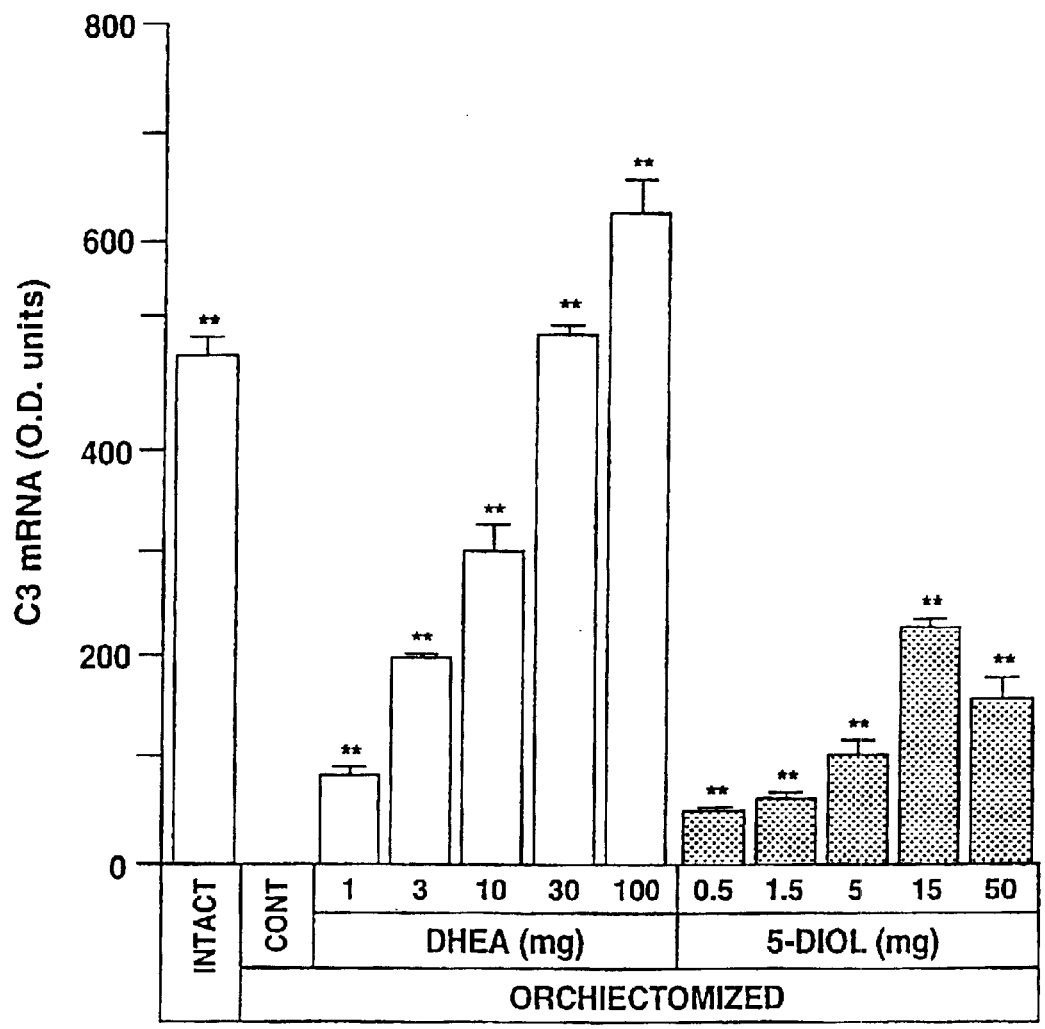
FIG. 11 is a graph of the effect of increasing doses of DHEA or 5-DIOL, administered percutaneously twice daily for 7 days, on the mRNA encoding the C3 component of prostatic binding protein. (PBP-C3) in the ventral prostate of orchiectomized rats, a measure of androgenic effect. Intact animals are used as additional controls.

FIGS. 10 and 11 confirm the relatively higher level of androgenic activity of DHEA as compared to the activity of 5-DIOL. The data shows, depending on dosage, that DHEA is two to five more potent than 5-DIOL in stimulating prostate binding protein-C1 (PBP-C1) and prostate binding protein-C3 (PBP-C3) mRNA levels. The levels of PSP-C1 and PBP-C3 mRNA are particularly sensitive parameters of androgenic action of the concentration of the mRNAs encoding these proteins is regulated by androgens. Measurements of PBP-Cl and PBP-C3 mRNA levels are indicative of the androgenic activity since androgens act at the transcriptional level to increase steady state levels of the mRNAs encoding the subunit components of PBP.

Because both DHEA and 5-DIOL administered percutaneously have almost identical effects on estrogenic parameters at a given dosage, DHEA produces two to three times more androgenic activity than 5-DIOL where equivalent estrogenic effects are provided.

Figure 3:
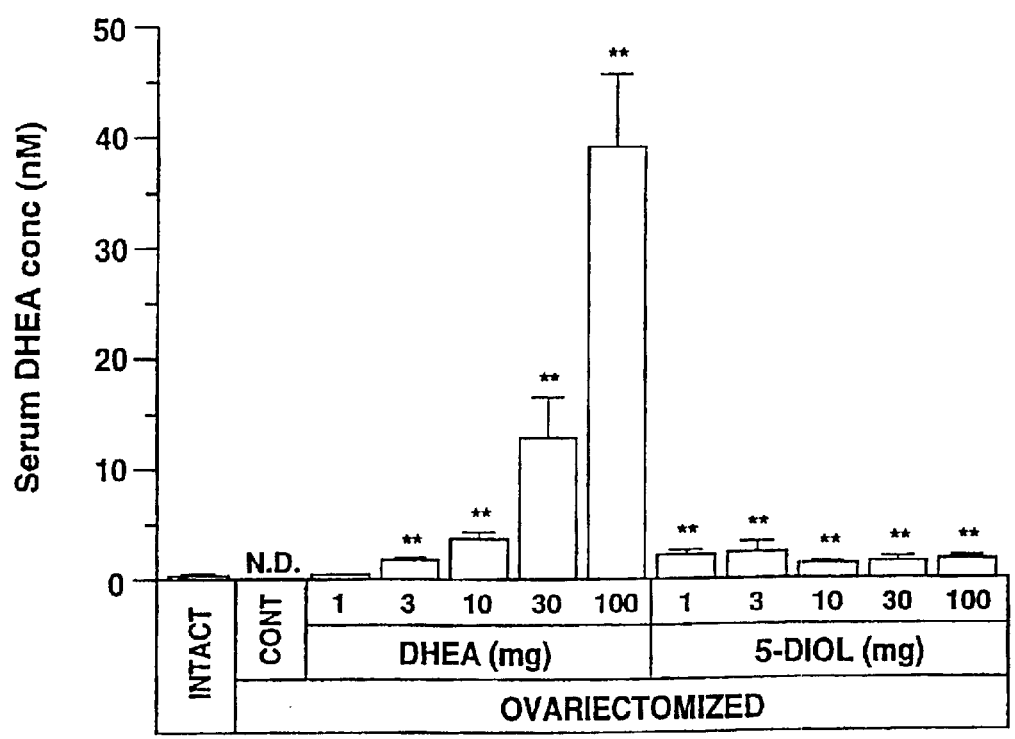
FIG. 3 is a graph of the effect of increasing doses of DHEA or 5-DIOL, administered percutaneously twice daily for 7 days, on the serum DHEA concentration in ovariectomized rats. Intact animals are used as additional controls. The compounds were dissolved in 50% ethanol–50% propylene glycol and were administered in 0.1 ml on the dorsal skin area (2 cm×2 cm).
Figure 4:
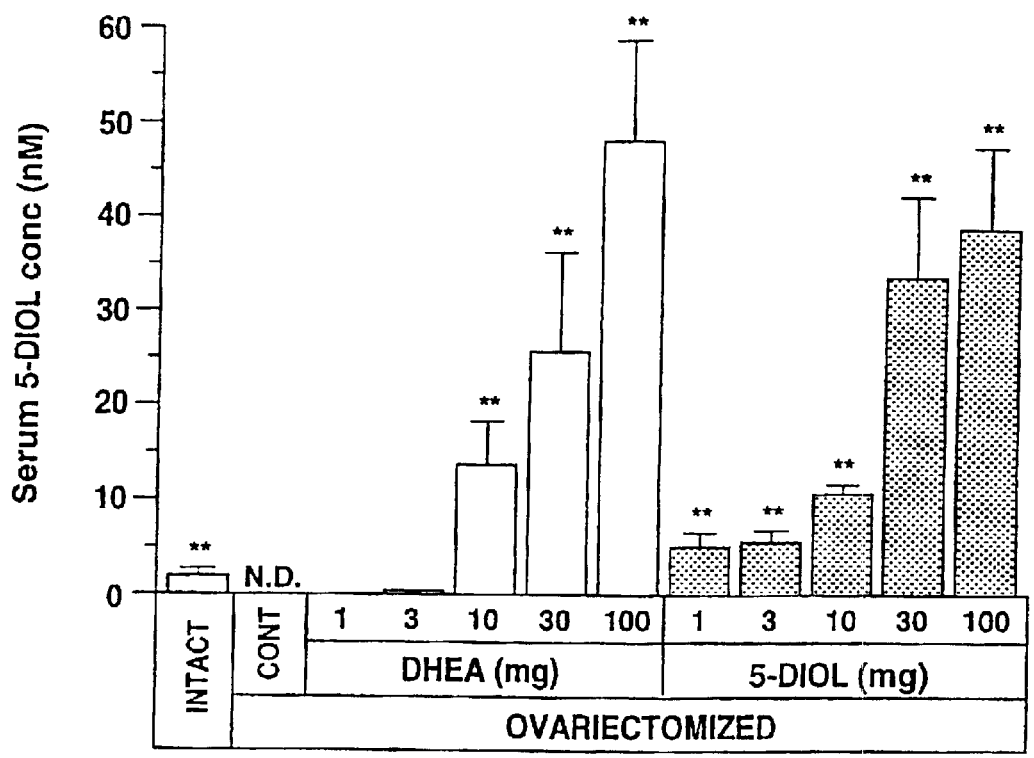
FIG. 4 is a graph of the effect of increasing doses of DHEA or 5-DIOL, administered percutaneously twice daily for 7 days, on the serum 5-DIOL concentration in ovariectomized rats. Intact animals are used as additional controls. The compounds were dissolved in 50% ethanol–50% propylene glycol and were administered in 0.1 ml on the dorsal skin area (2 cm×2 cm).

It has also been found that a major difference between DHEA and 5-DIOL is that oxidative 17β-HSD(s) which transform(s) 5-DIOL into DHEA has an extremely low level of activity after systemic administration of 5-DIOL (see FIGS. 3 and 4). On the other hand, the similar levels of serum 5-DIOL following administration of DHEA and 5-DIOL indicate that the reductive 17β-HSD has a relatively high level of activity. In addition, since no significant DHEA appears available to be transformed directly into 4-dione by 3β-HSD, following 5-DIOL administration, androstenedione must derive from the oxidation of testosterone. This is in agreement with the fact that levels of serum 4-dione, a highly efficient precursor of androgens, are much lower after 5-DIOL treatment than after DHEA treatment.

Without intending to be bound by theory, it is believed that one of the reasons DHEA produces a different androgenic response than does 5-DIOL (at equal dosage) is that DHEA and 5-DIOL are metabolized differently. 5-DIOL's metabolism (more so than DHEA's metabolism) leads to less formation and/or more inactivation of certain steriods (e.g. testosterone and DHT) before they can exert androgenic activity. Thus, 5-DIOL leads to lower exposure to these potent adrogens than does an equal dose of DHEA where the oxidized steroids predominate as a reservoir for formation of the active androgens.

Figure 14:
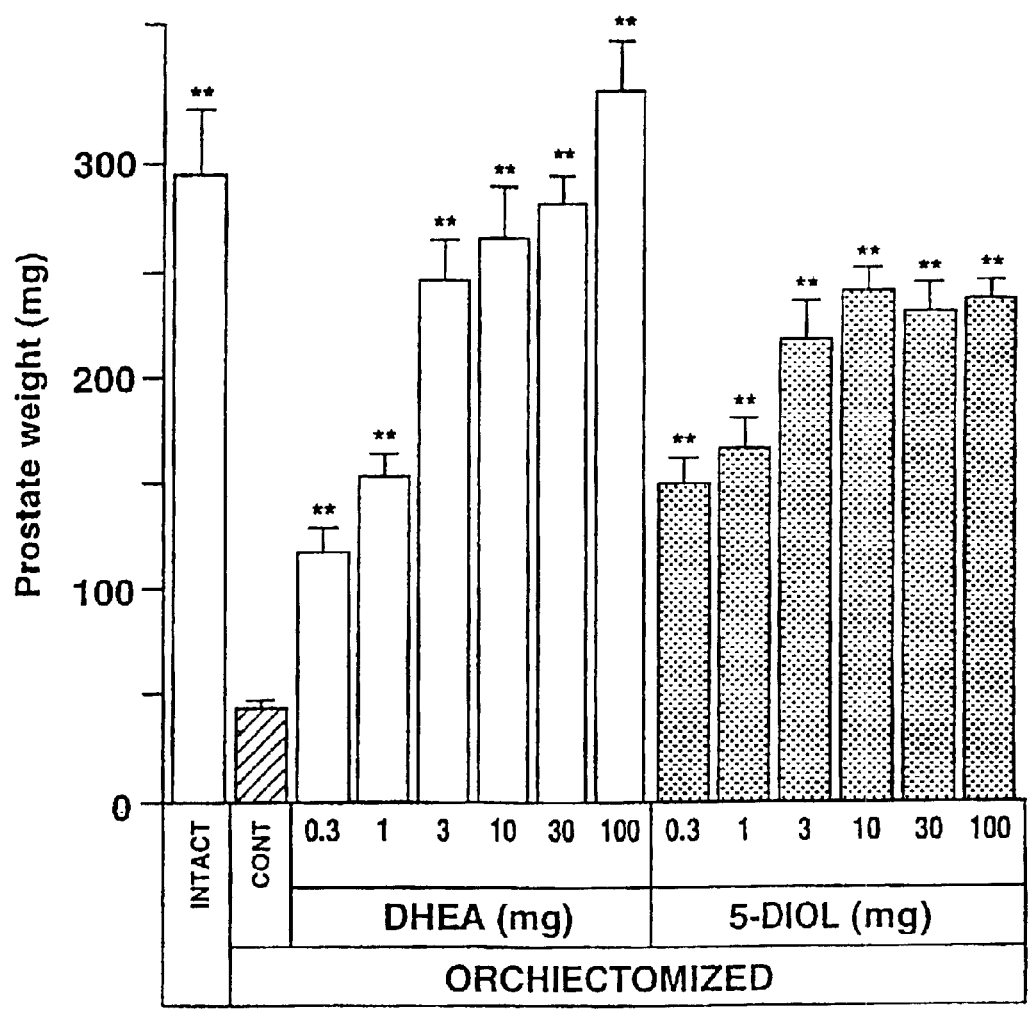
FIG. 14 is a graph of the effect of increasing doses of DHEA or 5-DIOL, administered subcutaneously twice daily for 7 days, on prostate weight in orchiectomized rats, a measured of androgenic effect. Intact animals are used as additional controls.
Figure 15:
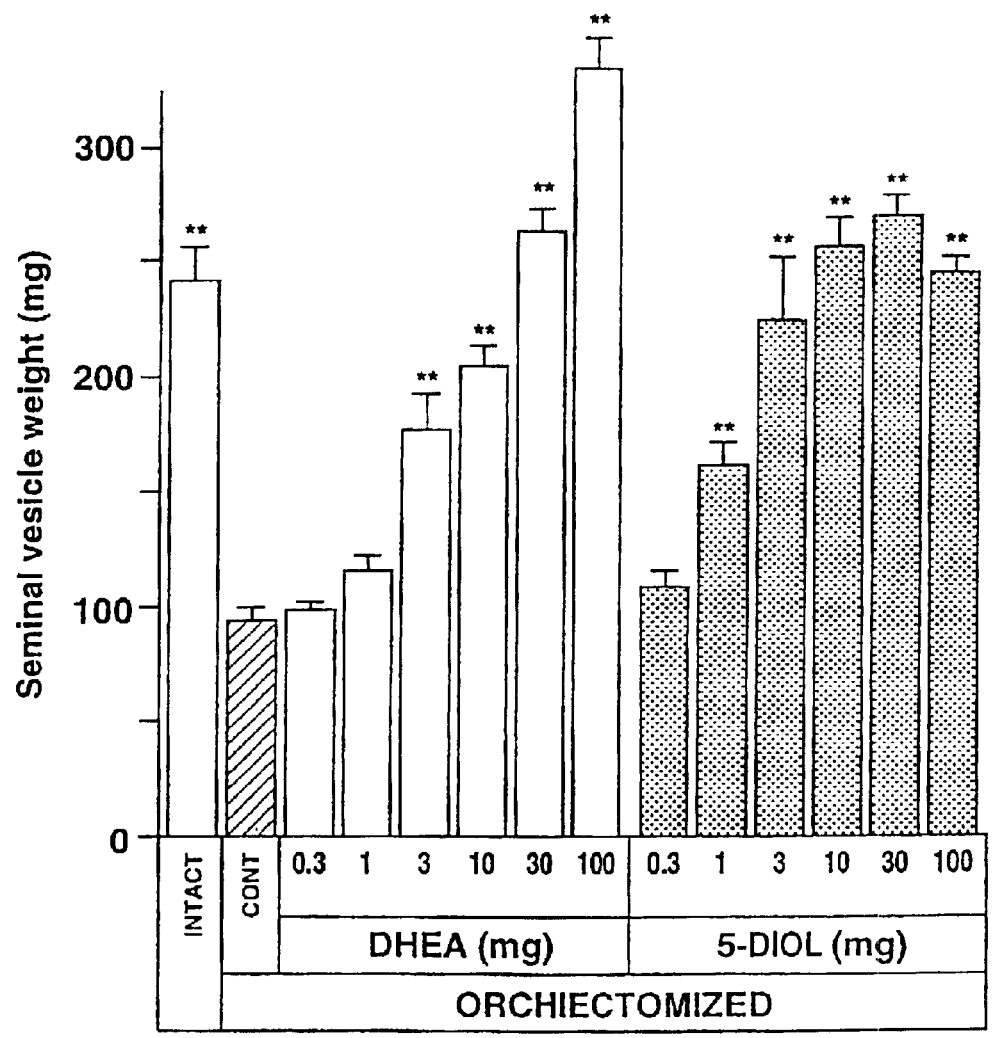
FIG. 15 is a graph of the effect of increasing doses of DHEA or 5-DIOL, administered subcutaneously twice daily for 7 days, on seminal vesicle weight in orchiectomized rats, a measure of androgenic effect. Intact animals are used as additional controls.

Further, as shown in FIGS. 14 and 15, where both compounds were administered by the subcutaneous route for an assessment of maximal bioavailability, the stimulation of androgen-sensitive parameters by 5-DIOL reached a plateau at a lower value than achieved with DHEA. It is thus clear that the difference of maximal androgenic activity of DHEA and 5-DIOL observed after percutaneous administration of the two compounds (FIGS. 8, 9, 10, and 11) is not due to different rates of absorption through the skin.

In general, the estrogenic activities of 5-DIOL under conditions of maximal bioavailability were shown to be greater than those of the same doses of DHEA. In fact, after subcutaneous administration, 5-DIOL is about 5 times more potent than DHEA to stimulate uterine growth. Therefore, as discussed above, at a dosage where the estrogenic effects are the same, the androgenic effects produced by 5-DIOL will be significantly lower than the effects produced by DHEA. Moreover, the androgenic effects of 5-DIOL reach a plateau of maximal effect which is significantly lower than the maximal stimulation achieved with DHEA.

As will be discussed in detail below, 5-DIOL can be administered to treat or prevent conditions in patients who have insufficient levels or imbalanced concentrations of sex steroids, namely androgens and/or estrogens. In particular, 5-DIOL is believed useful in treating and reducing risk of acquiring conditions which respond favorably to estrogenic activity and in which lower androgenic activity than provided by DHEA is desired. Because 5-DIOL is metabolized qualitatively to the same sex steroids as is DHEA, 5-DIOL may be used for any purpose that responds favorably to DHEA, with the benefit of different androgenic versus estrogenic effects than would result from using DHEA. Where the desired estrogen/androgen ratio lies between what is achievable with DHEA versus 5-DIOL, then a mixture of DHEA and 5-DIOL may be used to provide the desired ratio.

Individuals who will benefit from treatment with 5-DIOL include all those suffering from conditions treatable with DHEA, including those with abnormally low levels of 5-DIOL, estrogen, or androgen. Reducing the risk of acquiring such conditions is also possible and the recommended 5-DIOL dosage and target serum levels is the same as for the therapeutic uses of 5-DIOL herein. Individuals who could benefit from the invention can be identified by measuring serum levels of 5-DIOL, DHEA, sex steroids and their metabolites (especially androsterone glucuronide and androstane-3a,17β-diol glucuronide for androgens and estrone-sulfate and estradiol-sulfate for estrogens) as described by Bélanger et al., in Steroid Formation, Degradation and Action in Peripheral, Normal and Neoplastic tissues (H. Bradlow, L. Castagnetta, S. d'Aquino, L. Gogliotti, eds) Ann. N.Y. Acad. Sci. 586: 93–100, 1990. Serum IGF-1 levels can be measured as described (Furlanetto et al., J. Clin. Invest. 60: 648, 1977).

In accordance with one aspect of the invention, once the deficiency or imbalance is determined, 5-DIOL is preferably administered at a dosage sufficient to raise and maintain serum 5-DIOL concentrations up to 3 times above the normal range of young adults. Serum Concentrations of 5-DIOL between 4.0 nM and 10 nM for women and 10 to 20 nM for men are preferred, e.g. 7.0 nM for women and 15 nM for men. Naturally, the attending clinician may raise or lower dosage based on patient response which may vary significantly. Intermittent or continuous administration of a progestin (e.g. medroxyprogesterone acetate, 5 . 10 mg/day orally) may alleviate possible unwanted side effects on the endometrium of the 5-DIOL treatment in premenopausal women In some preferred embodiments, serum concentration is between 4.0 and 7.0 or between 7.0 and 15 nM for women and men, respectively. However, for purposes of contraception or for preventing of ovarian or uterine cancer, concentrations up to 15 nM (e.g. between 10 and 13) may be preferred for women. For contraception, an estrogen may be added (e.g. estradiol giving serum estradiol levels between 50 and 200 nanograms per liter), and an added progestin may be particularly appropriate. Preferred dosages discussed herein may be increased as appropriate to achieve desired serum concentrations, e.g. with variations for individuals patient response as monitored by the attending clinician.

When 5-DIOL is administered by the percutaneous or transmucosal technique, the delivered dosage may be raised or lowered in known ways, i.e. by altering the location to which the lotion, ointment, cream, gel or patch is applied by altering the size of the surface area to which it is applied, by altering the concentration of the active ingredient, or by altering the vehicle or carrier. For example, increasing the surface area will normally increase the dosage of active ingredient delivered if the concentration of active ingredient remains constant. In the same manner, dosage delivered increases with increased concentration of active ingredient in the delivery base, and decreases with decreased concentration. Dosage delivered into the bloodstream also varies in a known manner with respect to the body region at which the transdermal penetration system is applied to the skin. Changing the vehicle or carrier can also alter the delivered dosage in known ways.

Preferably, serum 5-DIOL concentration is measured before treatment begins, and a dosage is selected to quickly raise serum 5-DIOL concentration to the preferred target range between 4.0 and 10 nM for women and 10 to 20 nM for men. Subsequently, the patient is monitored both symptomatologically and by circulating 5-DIOL or sex steroid metabolite concentrations to verify that the desired serum concentration and symptomatic relief have been obtained. 5-DIOL is then maintained at a constant concentration in the circulation. For a typical postmenopausal patient, for example, this dosage is the equivalent of application of 400 mg of the 5-DIOL, as part of a 10 percent composition in 50% ethanol–50% propylene glycol, to a 200 square centimeter area of the abdomen or thighs two times daily per 50 kg of body weight. If oral administration is chosen, 500 mg should be administered twice daily per 50 kg of body weight.

As used in the invention, 5-DIOL may be administered with or without additional carrier or diluent by the oral route but requires an additional carrier or diluent when administered by the percutaneous or transmucosal route. In a pharmaceutical composition for oral administration, 5-DIOL is preferably present in a concentration between 5 and 99% by weight relative to total weight of the composition, more preferably between 50 and 99 percent, especially between 80 and 99 percent.

When prepared for percutaneous administration, 5-DIOL is preferably present in a concentration between 2 and 20% by weight relative to the total weight of the composition, more preferably between 5 and 15%, especially between 5 and 10%.

The 5-DIOL active ingredient may be obtained from Steraloids Inc. (P.O. Box 310, Wilton, N.H., 03086, USA). Preferred 5-diol prodrugs are the two compounds set forth below, commercially available from Steraloids Inc.

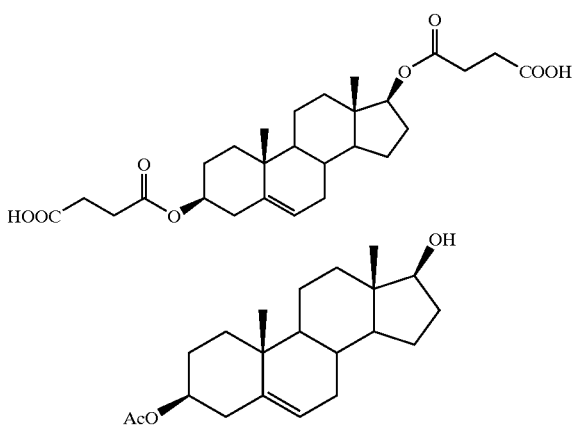

5-DIOL may be administered alone or may be administered in combination with other active compounds, such as antiestrogens, progestins, androgens, estrogens, DHEA or DHEA-S, inhibitors of 17β-hydroxysteroid dehydrogenase, aromatase inhibitors, LHRH agonists or antagonists and other inhibitors of gondal steroid secretion. Both DHEA and 5-DIOL are metabolized to androgens and estrogens, but in different proportions. In addition, 5-DIOL possesses weak intrinsic estrogenic activity. That, in conjunction with the different inherent action DHEA or 5-DIOL have on the androgen or estrogen receptor, is believed to impart the different ratios of androgenic versus estrogenic activity provided by 5-DIOL versus DHEA. It is not necessary to utilize only DHEA's androgen/estrogen ratio or only 5-DIOL's androgen/estrogen ratio. DHEA and 5-DIOL may be used together to provide an optimally effective androgenic/estrogenic response ratio that is between the ratio for DHEA and the ratio for 5-DIOL. The relative amounts of DHEA versus 5-DIOL may be varied depending on whether the desired androgen/estrogen response ratio lies closest to that of DHEA or to that of 5-DIOL.

For the treatment of breast cancer, endometrial cancer, ovarian cancer, endometriosis or other estrogen-sensitive disease requiring blockage of estrogen formation and/or action, at least one of the following, namely an antiestrogen, an aromatase inhibitor, an androgenic compound, a progestin, an LHRH agonist or antagonist or another inhibitor or gonadal sex steroid secretion, an inhibitor or 17β-hydroxysteroid dehydrogenase activity can be used in combination with 5-DIOL. 5-DIOL alone or with DHEA would provide the androgenic component required to stimulate androgen-sensitive functions, particularly bone formation and inhibition of androgen-sensitive cancer growth (e.g. breast and endometrial cancer). 5-DIOL could then be used alone or in combination with any of the compounds mentioned above useful in the combination. In some cases, DHEA in the absence of 5-DIOL could be used in combination with any of the compounds mentioned above.

In another embodiment, 5-DIOL is combined with an antiestrogen, which is preferably EM-800 ((−)-7-pivaloyloxy-3-(4'-pivaloyloxyphenyl)-4-methyl-2 (4'''-2(2-piperininoethoxy)phenyl)-2H-benzopyran), ICI 182,780 (7a-[9-4(4,4,5,5,5-pentafluoro-pentylsulphinyl)nonyl] oestra-1,3,5(10)-triene-3,17β-diol) or any other antiestrogen for the treatment of breast cancer, endometrial cancer, ovarian cancer, cardiovascular diseases, atherosclerosis, and other estrogen-sensitive, diseases. Non-steroidal antiestrogens such as EM-800 tend to be selective estrogen receptor modulators which act as estrogen receptor antagonists in breast tissue, yet provide estrogen-like beneficial effects on cholesterol, lipids and atherosclerosis.

The dosage of 5-DIOL can vary. The blood level of 5-DIOL and of other sex steroids and their metabolites is indicative of the adequate dosage taking into account individual variation in absorption, metabolism, and sensitivity of response. Preferably, the attending clinician will, especially at the beginning of treatment, monitor of individual patient's overall response and serum levels of 5-DIOL (in comparison to the preferred serum concentration discussed above), and monitor the patient's overall response to treatment, adjusting dosages as necessary where a given patient's metabolism or reaction to treatment is atypical. For combination therapies, one approach would be to start treating with 5-DIOL alone and to add the other compounds only if necessary. For treatment of breast cancer, endometrial cancer, ovarian cancer, and endometriosis, treatment with antiestrogen–5-DIOL or antiestrogen+5-DIOL+DHEA or antiestrogen+DHEA are started simultaneously. If DHEA, androgen, progestin or estrogen is added, similar monitoring of overall serum levels, both of the active ingredients and androgenic or estrogenic metabolites is preferred during early stages of treatment and as judged useful by the physician at later time intervals.

Treatment in accordance with the invention is suitable for indefinite continuation. It is expected that 5-DIOL treatment will usually simply maintain this natural steroid within a range of 4 to 10 nM and 10 to 20 nM serum concentration for women and men, respectively. Undesirable side effects from sustained 5-DIOL treatment are expected to be either minimal or nonexistent. Avoiding unlikely side effects from sustained estrogen use may be achieved in ways already known to the art, for example, by intermittent (or in some embodiments continuous) administration of a progestin (e.g. medroxyprogesterone acetate) at a daily oral dose of 2 to 10 mg. Any androgenic side effects should be minimal due to the relatively low androgenic effects of 5-DIOL and the already low levels of DHEA in most patients undergoing the method of the invention (FIG. 18).

In order to facilitate the combination therapy aspect of the invention, for any indication discussed herein, the invention contemplates pharmaceutical compositions which include both 5-DIOL and a second or subsequent active compound (s) in a single composition for simultaneous administration. The composition may be suitable for administration in any traditional manner including but not limited to oral administration, percutaneous administration or transmucosal administration. In other embodiments, a kit is provided wherein the kin includes 5-DIOL and a second compound in separate containers. Additional active compounds discussed herein may also be included. In addition to other modes of administration, the second compound as well as 5-DIOL may also be administered transdermally in accordance with the invention as discussed in more detail below. Thus, the kit may include appropriate materials for transdermal administration, e.g., ointments, lotions, gels, creams, sustained release patches and the like. The same strategy applies to the progestin, antiestrogen, androgen, estrogen, DHEA, DHEA-S, inhibitor of 17β-hydroxysteroid dehydrogenase, aromatase inhibitor or inhibitor of gonadal sex steroid secretion which can be administered orally (or by injection for the LHRH agonist or antagonist).

Although, it is anticipated that in some circumstances 5-DIOL may be administered by injection, this method is not favored. Since treatment with 5-DIOL will often be of prolonged and indefinite duration, repeated delivery by injection is inconvenient.

It is believed that the preferred routes for therapeutic administration of 5-DIOL are percutaneous, transmucosal or oral, since the discomfort and inconvenience of administering 5-DIOL by injection are avoided.

Any of a number of art-recognized transdermal penetration systems may be utilized for the delivery of 5-DIOL. For example, 5-DIOl may be prepared as part of an ointment, lotion, gel or cream for rubbing onto a patient's skin or mucosa. The active ingredient is preferably present from approximately 5% to 20% by weight relative to the total weight of the pharmaceutical composition and more preferably is between approximately 5 and 12% by weight. Alternatively, the active ingredient may be placed into a transdermal patch having structures known in the art, for example, structures such as those set forth in E.P. Patent No. 0279982.

When formulated as an ointment, lotion, gel, cream or the like, the active compound is admixed with a suitable carrier which is compatible with human skin or mucosa and which enhances transdermal or transmucosal penetration of the compound through the skin or mucosa. Suitable carriers are known in the art and include but are not limited to Klucel HF and Glaxal base which is available from Glaxal Canada Limited Company. Other suitable vehicles can be found in Koller and Buri, S. T. P. Pharm 3(2), 115–124, 1987. The carrier is preferably one in which the active ingredient(s) is(are) soluble at ambient temperature at the concentration of active ingredient that is used. The carrier should have sufficient viscosity to maintain the precursor on a localized area of skin or mucosa to which the composition has been applied, without running or evaporating for a time period sufficient to permit substantial penetration of the precursor through the localized area of skin or mucosa and into the bloodstream where it will cause measurable and desired increases in serum 5-DIOL concentration. The carrier is typically a mixture of several components, e.g. pharmaceutically acceptable solvents and a thickening agent. A mixture of organic and inorganic solvents can aid hydrophilic and lipophilic solubility, e.g. water and an alcohol such as ethanol.

Desirably, the carrier is one which, if formulated as 10% 5-DIOL and 90% carrier (by weight) and applied twice daily in an amount providing 100 mg of 5-DIOL to the abdominal area, it will elevate serum concentration of 5-DIOL in a typical patient by at least 1.0 nM per 50 kg of body weight above serum levels prior to treatment, and thereafter maintain relatively constant serum levels of 5-DIOL.

The carrier may include various additives commonly used in ointments, lotions, gel, and creams and well known in the cosmetic and medical arts. For example, fragrances, antioxidants, perfumes, gelling agent, thickening agents such as carboxymethylcellulose, surfactants, stabilizers, emolients, coloring agents and other similar agents may be present. When used to treat systemic diseases, the site of application on the skin is preferably changed periodically to avoid potential excess local concentration of steroids and possible overstimulation of the skin and sebaceous glands by androgenic metabolites of 5-DIOL.

5-DIOL or derivatives can also be administered, by the oral route, and may be formulated with conventional pharmaceutical excipients, e.g. spray dried lactose and magnesium stearate into tablets or capsules or oral administration at concentrations providing easy dosage in a range from 0.050 to 2.5 grams per day per 50 kg of body weight.

The active substance can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycol. Of course, taste-improving substances can be added in the case of oral administration forms. The active substance can be also administered in solid dispersion state in appropriate carriers. Such carriers may be chosen from the group consisting of polyethylene glycols of molecular weight varying from 1000 to 2000 and polyvinylpyrrolidone (Povidone purchased from American Chemicals Ltd., Montréal, Canada).

As further forms, one can use plug capsules, e.g. of hard gelatin, as well as closed soft-gelatin capsules comprising a softener or plasticized, e.g. glycerine. The plug capsules contain the active substance preferably in the form of granulate, e.g. in mixture with fillers, such as lactose, saccharose, mannitol, starches, such as potato starch or amylopectin, cellulose derivatives or highly dispersed silicic acids. In soft-gelatin capsules, the active substance is preferably dissolved or suspended in suitable liquids, such as vegetable oils or liquid polyethylene glycols.

The concentration of active ingredients in the ointment, cream, gel or lotion is typically from about 2 to 20 percent preferably between 5 and 15 percent and preferably between 5 and 10 percent (by weight relative to the total weight of the lotion, cream, gel or ointment). Within the preferred ranges, higher concentrations allow a suitable dosage to be achieved while applying the lotion, ointment, gel or cream to a lesser surface area of the skin than would be possible at lower concentrations and allow more freedom in choosing the body parts to which the ointment or lotion will be applied. For example, it is well known in the art that a compound which is capable of transdermal penetration normally penetrates more efficiently at some points in the body than in others. For example, penetration is very efficient on the forearm and considerably less efficient on the palms.

The lotion, ointment, gel or cream should be thoroughly rubbed into the skin so that no excess is plainly visible, and the skin would not be washed in that region until most of the transdermal penetration has occurred, preferably, at least 15 minutes and, more preferably, at least 30 minutes after application.

A transdermal patch may be used to deliver 5-DIOL in accordance with known techniques. It is typically applied for a much longer period, e.g. 0.5 to 4 days, but typically contacts active ingredients to a smaller surface area, allowing a slow and constant delivery of active ingredient.

A number of transdermal drug delivery systems that have been developed, and are in use, are suitable for delivering the active ingredient of the present invention. The rate of release is typically controlled by a matrix diffusion, or by passage of the active ingredient through a controlling membrane.

Mechanical aspects of transdermal devices are well known in the art, and are explained, for example, in U.S. Pat. Nos. 4,162,037, 5,154,922, 5,135,480, 4,666,441, 4,624,665, 3,742,951, 3,797,444, 4,568,343, 4,064,654, 5,071,644, 5,071,657, the disclosures of which are incorporated herein by reference. Additional background is provided by European Patent 0279982 and British Patent Application 2185187.

The device may be any of the general types known in the art including adhesive matrix and reservoir-type transdermal delivery devices. The device may include drug-containing matrixes incorporating fibres which absorb the active ingredient and/or carrier. In a reservoir-type device, the reservoir may be defined by a polymer membrane impermeable to the carrier and to the active ingredient.

In a transdermal device, the device itself maintains active ingredient in contact with the desired localized skin surface. In such a device, the viscosity of the carrier for active ingredient is of less concern than with a cream or gel. A solvent system for a transdermal device may include, for example, oleic acid, linear alcohol lactate and dipropylene glycol, or other solvent systems known in the art. The active ingredient may be dissolved or suspended in the carrier.

For attachment to the skin, a transdermal patch may be mounted on a surgical adhesive tape having a hole punched in the middle. The adhesive is preferably covered by a release liner to protect it prior to use. Typical material suitable for release includes polyethylene and polyethylene-coated paper, and preferably silicone-coated for ease of removal. For applying the device, the release liner is simply peeled away and the adhesive attached to the patient's skin. In U.S. Pat. No. 4,135,480, the disclosure of which is incorporated by reference, Bannon et al. described an alternative device having a non-adhesive means for securing the device to the skin.

Except for the higher dosage indications noted above (e.g. contraception), the target serum concentration of 5-DIOL is comparable regardless of whether 5-DIOL is being used as part of a combination therapy for treatment of menopause or is being used (by itself or in combination with antiestrogens, androgens, progestins, estrogens and inhibitors of 17β-hydroxysteroid dehydrogenase, aromatase inhibitors, inhibitors of gonadal sex steroid formation, LHRH agonists or antagonists, DHEA and/or DHEA-S) for the treatment of cardiovascular diseases, osteoporosis, skin deterioration, menopause, vaginal atrophy, urinary incontinence, uterine cancer, ovarian cancer, osteoporosis, endometriosis, hypogonadism or diminished libido in accordance with the invention or for the treatment of any conditions related to decrease or imbalances in the levels of sex steroids, in particular 5-DIOL and its metabolites.

5-DIOL is particularly useful in treating conditions in which a minimal androgenic effect is desired since the androgenic effects of 5-DIOL are lower than produced by DHEA for an equal estrogenic effect and the maximal androgenic effect achieved with 5-DIOL is lower than that achieved with DHEA. 5-DIOL is especially preferred for the treatment of conditions in women that respond to estrogen therapy (or therapy with an estrogen precursor, such as DHEA) since the androgenic action of 5-DIOL is lower than that of DHEA and therefore, the potential androgenic or masculinizing effects are reduced, while the desired estrogenic activity is provided. Moreover, in postmenopausal women, in general a greater estrogenic/androgenic ratio than that provided by DHEA is required.

Figure 17:
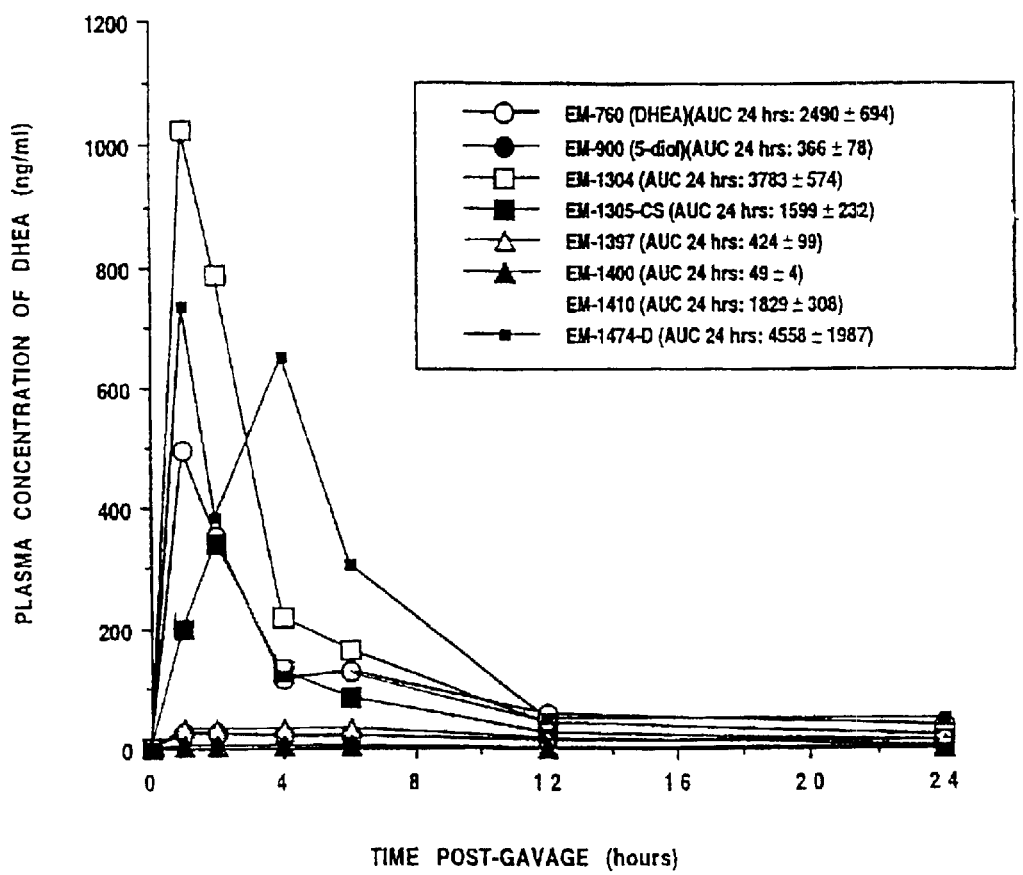
FIG. 17 shows the plasma concentrations of DHEA (ng/mL) (Y axis in function of time (X-axis) after a single oral absorption of prodrugs of andros-5-ene-3β,17β-diol (150 μmol/rat) in male rats. In the box, AUC 24h of DHEA induced by these compounds is reported.

Since 5-DIOL is a natural source of estrogens and androgens and the secretion of this compound markedly decreases during aging (FIG. 17), its replacement should have minimal unwanted side effects. Its intrinsic estrogenic activity should compensate for the loss of estrogen secretion by the ovaries after menopause, an effect not achievable by DHEA. The invention is useful for many diseases wherein activation of the estrogen receptor will have beneficial effects, especially osteoporosis and menopausal symptoms, including vaginal atrophy, insomnia, irritability, cardiovascular disease, urinary incontinence, and loss of libido. In addition, the invention is useful for treating and preventing diseases which are responsive to the activation of the androgen receptor, e.g. bone loss, obesity, breast cancer, endometrial cancer, ovarian cancer, urinary incontinence, hypogonadism, loss of libido, loss of muscle mass, loss of energy, insulin resistance and other aging processes. Further, 5-DIOL can be used to treat or prevent any condition which responds favorably to an improvement in the overall balance of circulating sex steroids, namely estrogens and androgens.

Conditions expected to respond to the treatments herein may be diagnosed in conventional ways. For example, the appearance of breast cancer is usually detected by self breast examination, clinical breast examination by the physician and/or mammography. Endometrial cancer, on the other hand, is usually diagnosed by endometrial biopsy. Both cancers can be diagnosed and evaluated by standard physical methods well known to those skilled in the art, e.g. bone scan, chest X-Ray, skeletal survey, ultrasonography of the liver and liver scan (if needed), CAT scan, MRI and physical examination.

The onset of menopause is generally first recognized by the occurrence of hot flashes. Further characterization of the menopause can be determined in accordance with known techniques. See for Example, The Menopause (Herbert J. Buchsbaurm, ed), Springer Verlag, New York (1983), pp. 222. Vaginal atrophy is often indicated by dyspareunia and vaginal infections. Vaginal atrophy, hypogonadism, diminished libido, insomnia, irritability, depression, and urinary incontinence are all characterized in well-known ways. For the above-indicated disease, see, for example, Korenman, Stanley G, "Sexual Dysfunctions" in Williams Textbook of Endocrinology, Jean D. Wilson and Daniel W. Foster, eds), WB Saunders Co., Philadelphia, pp. 1033–1048, 1992.

Bone density, on the other hand, can be measured by standard methods well known to those skilled in the art, e.g. QDR (Quantitative Digital Radiography), dual photon absorptiometry and computerized tomography. Plasma and urinary calcium and phosphate levels, plasma alkaline phosphatase, osteocalcin, calcitonin and parathormone concentrations, as well as urinary hydroxyproline, deoxypyrrolidine, and calcium/creatinin ratios are useful parameters of bone formation and resorption.

Loss of collagen or connective tissues in the skin often accompanies aging, especially in persons over 50 years of age. It may be evidenced by wrinkling of the skin and/or low elasticity. Skin status can be accessed by visual inspection, palpation and, with more precision, by punch biopsy and standard histological examination.

The normal range of body weight is well known to those skilled in the art, while cholesterol and lipoproteins are routinely measured by standard techniques (Nestler et al. J. Clin. Endocrinol. Metab. 66: 57–61, 1988 for references).

In addition, 5-DIOL is useful as a female contraceptive. In the prior art, female contraception usually involves administering an estrogen, which at increased circulating levels, reduces LHRH secretion from the hypothalamus which, in turn, decreases LH secretion from the pituitary. The resultant reduction in LH secretion decreased ovarian function, and in particular ovulation. Addition to a progestin controlled the growth of the endometrium and transformed the vaginal and cervical secretions into an unfavorable environment for sperm capacitation and fertility.

In the present invention, 5-DIOL provides estrogen for contraception while simultaneously and desirably providing minimally increased levels of androgens which will contribute to contraception since androgens also inhibit LHRH and LH secretion. These androgen can, especially in women at perimenopause (as well as in postmenopausal women when contraception is no longer required), provide much needed stimulation of bone formation and resistance to bone loss. In addition to being a weak estrogen by itself, the estrogens produced from the administered 5-DIOL also contribute to reducing bone loss. As with other uses discussed herein, use of 5-DIOL instead of a sex steroid (here estrogen) avoids externally administering relatively high doses of estrogens and this avoids giving such estrogens extensive access to all tissues, many of which do not require estrogens. By substituting 5-DIOL, estrogens and/or androgens are instead produced by natural processes in the same tissues where estrogens and/or androgens are needed and that normally convert 5-DIOL to estrogens and/or androgens. The relative proportions of estrogen and androgen also remain substantially at natural levels in each specific tissue.

Because ovarian function is diminished by the contraception technique described herein, the ovarian production of estrogen and progesterone will be decreased. Thus, a progestin (e.g. medoxyprogesterone acetate, megastrol acetate, norethynodrel, L-norgestrel) may be administered as part of the contraceptive method to prevent endometrial hypertrophy with high doses of 5-DIOL are needed. The progestin may be administered in a pharmaceutical composition that includes the 5-DIOL or separately. In certain embodiments, the progestin may be administered intermittently every month for 12–14 days, or 12–14 days every few months (e.g. every 2–5 months) or continuously, depending upon the dose of 5-DIOL used which may well have not stimulatory effect on the endometrium at physiological dose. Progestin dosage may be in the range utilized in the prior art but is preferably lower for reasons explained below.

Since 5-DIOL is converted to estrogen in many tissues, it is unlikely that estrogen will need to be added to the contraceptive therapy to compensate for the decreased estrogen production in the ovaries. However, minimum doses can be given, if necessary. Preferred dosage of added estrogen, when used in the contraceptive method is an amount effective to achieve between 50 and 300 nanograms estradiol per liter or equivalent. Preferably the ratio of added estradiol to 5-DIOL (w/w) will range from 100:1 to 10,000:1, preferably 200:1 to 5,000:1 and especially 300:1 to 3000:1. As with added progestin, added estrogen may be administered as part of a pharmaceutical composition that includes the 5-DIOL (or, when used, a prodrug of 5-DIOL) or separately.

In some embodiments, 5-DIOL, progestin and estrogen are all administered, together or separately, as part of a combination therapy. A combination therapy results whenever a regimen of treatment elevates blood levels of each active agent simultaneously. This simply requires that the active agents be administered sufficiently close in time that elevated blood levels of these agents are concurrent.

The use of combination contraceptives containing estrogens and progestins has not been shown to reduce the risk of breast cancer (Romiev et al., 1990, Cancer 66: 2253–2263). These data are consistent with a known mitogenic effect of both estrogen and progesterone on breast cell epithelial proliferation, thus explaining a peak of cell proliferation at mid-luteal phase (Masters et al., J. Natl. Cancer Inst. 1977, 58: 1263–1265; Anderson et al., 1982, Brit. J. Cancer 46 376–382). In fact, total breast cell proliferation rate in premenopausal women using contraceptives is not different from that of untreated cycling women (Potter et al., 1988; Brit. J. Cancer 58: 163–170; Going et al., 1988; Am. J. Pathol. 130: 193–204). The androgenic component of 5-DIOL should reduce this potential harmful effect of estrogens and progestins.

Osteoblasts (bone forming cells) contain the enzymes which convert 5-DIOL to estrogens and androgens. Therefore, 5-DIOL can be used instead of (or in addition to) androgen, estrogen, or DHEA in the treatment or prevention of osteoporosis. Sufficient quantities of androgens are produced in the bone (by conversion of the administered 5-DIOL) to stimulate bone formation and reduce bond loss. Furthermore, the low estrogenic activity of 5-DIOL and the estrogens produced from the administered 5-DIOL contribute to reducing bone loss.

Since bone mass density has been shown to be stimulated at particularly low doses of androgens, 5-DIOL, which has a lower ratio of anydrogenic/estrogenic activity than DHEA should be able to have maximal beneficial effects on the bone at a dosage which produces minimal risks of hyperandrogenism.

In addition, since 5-DIOL (or prodrugs thereof, if desired) is transformed to androgens and estrogens only by natural mechanisms exclusively in tissues that normally perform such transformation according to their local needs, side effects are greatly reduced or eliminated relative to externally administered active sex steroids of the prior art which have access to many tissues that neither produce nor require a given androgen or estrogen. The physiological balance of sex steroids in those tissues are thus not disturbed in accordance with the present invention, contrary to all hormone replacement therapies of prior art. The relative ratio of androgens and estrogens produced from the 5-DIOL is also a substantially normal ratio instead of being an abnormally elevated ratio of one type of sex steroid as occurs when that active sex steroid is directly administered exogenously, thus causing exposure of all tissues, including those having no need for such therapy.

In one preferred treatment for menopausal symptoms, the invention seeks to simultaneously maintain blood levels of 5-DIOL, androgens, and estrogens within normal premenopausal parameters. Without intending to be bound by theory, it is believed that maintenance of appropriate precursor levels will better enable natural enzymes, such as 17β-hydroxysteroid dehydrogenase, 3β-hydroxysteroid hydrogenase, aromatase and 5α-reductase to regulate production of androgens and estrogens and to maintain them in a manner more closely resembling their absolute and relative levels prevailing prior to menopause. Hence, the invention contemplates that not only estrogens but also androgens will be kept in better balance. In fact, the target tissues possess the enzymatic machinery necessary to synthesize and inactivate androgens and/or estrogens according to local needs (Labrie, Mol. Cell Endrocrinol. 78, C113–C118, 1991).

As discussed above, 5-DIOL can be administered with estrogens. However, since compared to DHEA, a relatively higher proportion of estrogens than androgens are produced and 5-DIOL is itself a weak estrogen, it should be possible to attain the desired level of estrogens without the addition of estrogens and without producing unwanted androgenic side effects accompanying high levels of DHEA, a more androgenic compound. Similarly, since 5-DIOL is a weak estrogen, progestin therapy may not be required.

However, if it is determined that additional estrogens are needed, the estrogen and 5-DIOL may be administered simultaneously or separately. In addition, it is necessary only that both the 5-DIOL and estrogen be administered in a manner and at a dosage sufficient to allow blood serum concentration of each to obtain desired levels. In accordance with the combination therapy of the invention, concentration of the 5-DIOL is maintained within desired parameters at the same time that estrogen concentration is maintained within desired parameters. Where estradiol is used, serum estradiol concentration should typically be maintained between 50 and 200 nanograms per liter, preferably between 100 and 175 nanograms per liter and most preferably between 125 and 175 nanograms per liter. Where another estrogen is used, serum concentration may be varied in a known manner to account for the known difference in estrogenic activity relative to estradiol and in order to achieve normal premenopausal estrogen levels. A lesser concentration is needed, for example, if Mestranol is used. Adequate serum estrogen levels can also be assessed by disappearance of the symptoms of menopause. Serum concentration of the 5-DIOL is typically maintained between 4 and 10 nM for women and between 10 and 20 nM for men or in some embodiments between 4.0 and 7.0 nM for women or between 7.0 and 15 nM for men.

If estrogen is combined with 5-DIOL, it is preferably estradiol, but may be estrone sulfate or another compound which acts as an estrogen receptor agonist directly or following proper conversion. When administered separately, commercially available estrogen supplements may be used, e.g., PREMARIN, available from Ayerst (St. Laurent, Québec, Canada). For typical patients, the appropriate dosage of estrogen to achieve desired serum concentrations is between 0.3 and 2.5 milligrams of PREMARIN per day 50 kg of body weight when administered orally. In certain embodiments of the invention, the estrogen may be 17β-estradiol administered percutaneously in a patch which is available from CIBA under the name ESTRADERM wherein the daily doses is between 0.05 and 0.2 milligrams per day per 50 kg of body weight. For typical patients, the appropriate dosage of the sex steroid percursor 5-DIOL to achieve desired serum concentration of the precursor is between 0.10 and 2.5 grams per day per 50 kg of body weight when administered orally. Other prodrugs will be administered at a dosage that depends on their in vivo conversion rate to 5-DIOL. 5-DIOL may also be administered transdermally or transmucosally, as described in detail above, in a sufficient amount to achieve target serum concentration.

In another embodiment, menopause is treated with 5-DIOL as set forth above, in combination with periodic administration of a progestin such as medroxyprogesterone acetate (e.g., Provera) which is preferably administered intermittently, e.g. at a dosage of 2–10 mg per day for 12 consecutive days, said 12-day periods being spaced 20 days to 5 months apart. A combination therapy using 5-DIOL, an estrogen and a progestin may also be used, preferably at the dosages discussed herein for each component.

The same doses of 5-DIOL will be used for all indications, except contraception and prevention of ovarian and endometrial cancer where serum levels of about to 15 nM 5-DIOL will be preferred.

For all other indications when androgens and/or estrogens are needed, the usual dosage mentioned above will be used. Similarly, when used in combination with an antiestrogen for the treatment or prevention of breast cancer, endometriosis, as other estrogen-sensitive disease, the same dose of 5-DIOL will be used. In some cases, where an aromatase inhibitor, an inhibitor of 17β-hydroxysteroid dehydrogenase, an androgen, a progestin, an inhibitor of gonadal steroid formation, an LHRH agonist or antagonist is used, the same dose of 5-DIOL is recommended.

The following examples demonstrate the androgenic and estrogenic effects of 5-DIOL and provide a comparison of the relative activities of 5-DIOL and DHEA. As discussed above, the preferential estrogenic activity relative to androgenic activity of 5-DIOL compared to DHEA is shown.

Materials and Methods

Animals

Male and female Sprague-Dawley rats [Crl:CD(SD)Br] weighing 225–250 g and 175–200 g, respectively, were obtained from Charles River Canada Inc. (St-Constant, Québec) and housed 2 per cage under a regimen of 14 h of light/day (lights on at 07:15 h). Animals received Purina rat chow and water ad libitum. The animal studies were conducted to the "Guideline for Care and Use of Experimental Animals".

Treatment

The animals were randomly divided into the indicated groups (8 and 10 rats per group for subcutaneous and topical administration, respectively). The animals of the appropriate groups were bilaterally ovariectomized (OVX) or orchiectomized (ORCH) under ether anesthheisa while other rats were used as intact controls. DHEA and 5-DIOL obtained from Steraloids (Wilton, N.H., USA) were dissolved in 50% ethanol-50% propylene glycol and applied twice daily (0.5 ml) on the dorsal skin area (2 cm×2 cm) for 7 days starting on the day of OVX or ORCH. For subcutaneous administration, DHEA and 5-DIOL were dissolved in 0.5 ml 10% ethanol-1% gelatin-0.9% NaCl and injected twice daily in the dorsal area for 7 days starting also on the day of OVX or ORCH.

Seven days after starting treatment or approximately 12 h after last administration of the steroid, the animals were killed by decapitation. Blood samples were collected individually and serum was frozen at −20° C. until assayed. Uteri, ovaries, ventral prostates, dorsal prostates and seminal vesicles were immediately removed, free from connective and adipose tissue, weighed, frozen in liquid nitrogen, and stored at −80° C. until assayed. Three rats from the indicated treatment groups were perfused with paramformaldehyde for in situ hybrization.

Steroid Analysis

Steroid extraction. Ethanol (5 ml) was added to 1 ml serum and centrifugation at 2000×g was performed for 15 min. The resulting pellet was further extracted with 2 ml ethanol and, after a second centrifugation at 2000×g for 15 min, the two supernatants were combined. The suspension was recentrifuged ass described above and the supernatant was decanted and combined with the previously obtained ethanol extracts. The organic solvent was then evaporated under nitrogen and the residue was dissolved in 1 ml water:methanol (95:5, v/v). The C-18 columns (Bound-Elut, Amersham, Bucks, U.K.) were conditioned by passing consecutively 10 ml methanol, 10 ml water and 10 ml methanol/water (5:95, v/v). The extracts solubilized in water:methanol (95:5, v/v) were then deposited on the C-18 columns. After washing the columns with 2 ml water:methanol (95:5, v/v) and 5 ml methanol:water (50:50, v/v), 5 ml methanol:water (85:15, v/v) were added to eluate the non-conjugated steroids.

Chromatography on LH-20 Columns and Radioimmunoassay

Chromatography on Sephadex LH-20 columns (Pharmacia, Uppsala, Sweden) was performed as previously described (Bélanger et al., 1988). In brief, steroids were solubilized in 1 ml isooctane/toluene/methanol (90:5:5, v:v:v) and deposited on the LH-20 columns. Fractions were collected and, after evaporation of the organic solvent, the concentration of the various steroids was determined by radioimmunoassay as previously descried (Bélanger et al., 1980; Bélanger et al., 1988; Bélanger et al., 1990).

Preparation of the cDNA Probes

The plasmid containing the DNA fragment complementary to the mRNA encoding PBP-Cl was kindly provided by Dr. Malcolm G. Parker (Imperial Cancer Research Fund, London, United Kingdom). The 434-basepair Pst-I restriction fragment of the PBP-Cl cDNA was purified by electroelution ((Bio-Rad electro-eluter, model 422, Bio-Rad, Richmond, Calif.; after electrophoresis on a 5% (wt/vol) polyacrylamide gel. The purified fragment was radiolabeled with [a-$^{35}$S]dCTPaS (Amersham, Oakville, Ontario, Canada) to high specific activity ($10^9$ dpm/μg) by the random primer method (Feinberg and Vogelstein, 1983).

Measurement of PBP-Cl mRNA Levels by in situ Hybridization

In situ hybridization of prostatic sections with the PBP-Cl probe was performed as described previously (Pelletier et al., 1988). In brief, rats were perfused with fixation buffer consisting of 4% paraformaldehyde in 0.1M phosphate buffer (pH 7.4). The ventral prostates freed from fat and connective tissue, were postfixed in fixation buffer for 2 h at 4 C and subsequently soaked in 0.05 M PBS containing 15% (wt/vol) sucrose. Thereafter, the ventral prostates were rapidly frozen in isopentane chilled in liquid nitrogen. Multiple (six to eight) 10 μM tissue sections from each ventral prostate were mounted on gelatin-coated glass slides. Prehydridization buffer contained 50% formamide, 5×SSPE (1×SSPE=0.18 M NaCl, 10 mM NaH$_2$PO$_1$, and 1 mM EDTA, pH 7.4), 0.1% sodium dodecyl sulfate, 0.1% BSA, 0.1% Ficoll, 0.1% polyinyl pyrrolidone, 0.2 mg/ml yeast tRNA, 0.2 mg/ml denatured salmon tests DNA, and 2 μg/ml poly(A). The slides were hybridized in prehybridiazation buffer containing, in addition, 4% dextran sulfate and saturating concentrations (1.0–1.5×$10^7$ cpm/ml) of the PSP-Cl cDNA probe for 48 h at 37° C. The sections were then washed twice for 30 min in 2×SSC (1×SSC=0.15 M NaCl and 0.015 M sodium citrate, pH 7.0, dehydrated, and exposed for autoradiography. To determine the amount of nonspecific background hybridization, prostatic sections for each treatment group were treated with pancreatin ribonuclease-A (20 μg/ml) for 1 h at room temperature before prehybridizing sections from rat brain, pituitary, kidney, and liver with the PBP-Cl probe. No specific hybridization could be observed (data not shown).

LH Radioimmunoassay

Serum LH was measured by double-antibody radioimmunoassay using rat hormones (LH-I-5 for iodination; LH-RP-2 as standard), and the rabbit antisera anti-r-LH-S-8, generously supplied by the National Pituitary Program, Baltimore, USA.

Statistical Analyses

Radioimmunoassay data were analyzed using a program based on model II of Rodbard and Lewald (Rodbard, 1974). Plasma steroid levels are shown as the means±SEM of duplicate determinations of individual samples. In situ hybridization data were obtained as follows: for each prostatic tissue section, 20 randomly selected areas measuring 0.25 mm$^2$ (excluding acinar lumen) were analyzed using an Image Research Analysis System (Amersham, Arlington Heights, Ill.), and the mean optical density value for each section was calculated. Data are shown as the means±SEM of 20 readings from 6–8 prostatic sections originating from ventral 3 prostates. Statistical significance was measured according to the multiple range test of Duncan-Kramer (Kramer, 1956).

Figure 1:
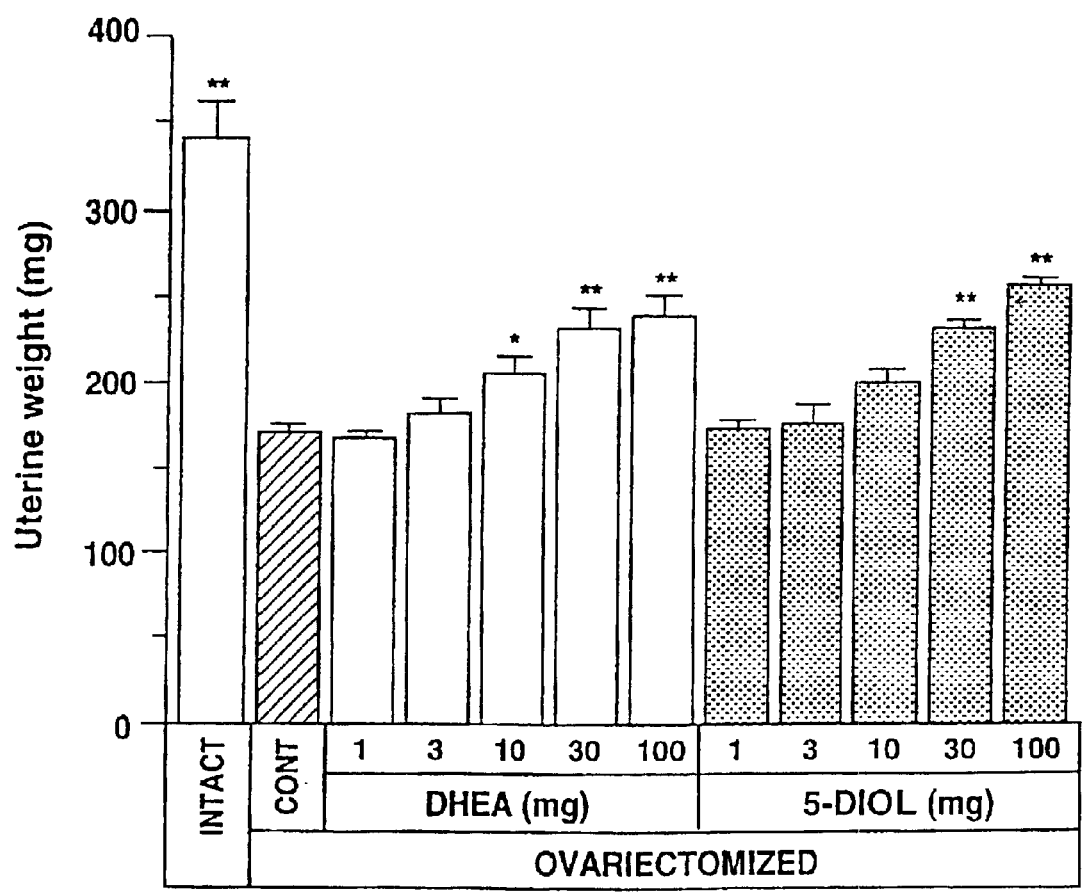
FIG. 1 is a graph of the effect of increasing doses of DHEA or 5-DIOL, administered percutaneously twice daily for 7 days, on the uterine weight in ovariectomized rats, an estrogen-sensitive parameter. Intact animals are used as additional controls. The compounds were dissolved in 50% ethanol–50% propylene glycol and were administered in 0.1 ml on the dorsal skin area (2 cm×2 cm).

As shown in FIG. 1, DHEA and 5-DIOL produced similar stimulatory effects on uterine weight, an indicator of estrogenic activity. In particular, the administration of the 10 mg and 30 mg doses of DHEA and 5-DIOL produced a comparable stimulation of uterine weight in the ovariectomized rat, while 1 and 3 mg doses had no significant effect. However, at 100 mg, the highest dose used, 5-DIOL produced a greater stimulatory effect with a maximal 52% reversal of the inhibitory effect of the ovariectomy as compared to the maximal 42% reversal produced by DHEA.

Figure 2:
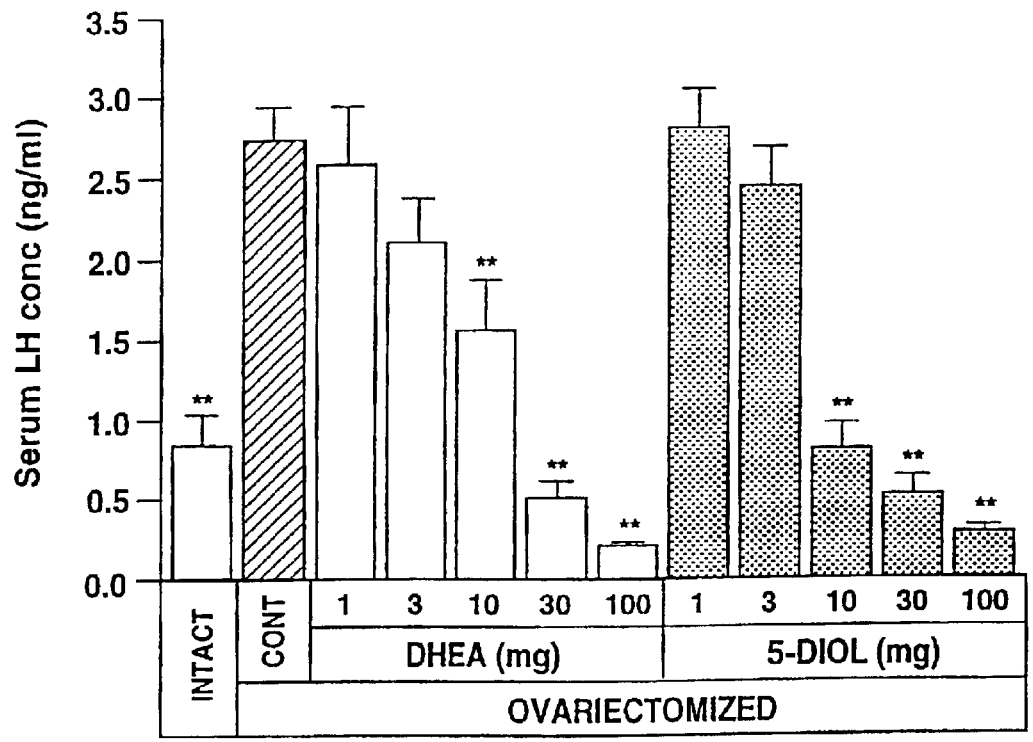
FIG. 2 is a graph of the effect of increasing doses of DHEA or 5-DIOL, administered percutaneously twice daily for 7 days, on the serum luteinizing hormone (LH) concentration in ovariecromized rats, a measure of androgenic and/or estrogenic effect. Intact animals are used as additional controls. The compounds were dissolved in 50% ethanol–50% propylene glycol and were administered in 0.1 ml on the dorsal skin area (2 cm×2 cm).

The effects of 5-DIOL and DHEA on serum LH are shown in FIG. 2. Serum LH is known to be a sensitive indicator of both androgenic and estrogenic activity based on the findings that serum LH increases rapidly upon the removal of the predominant inhibitory feedback action of sex steroids after gonadectomy in male as well as female animals (Ferland et al., In: Labrie, F., Meites, J., and Pelletier, G. (eds), Hypothalamus and Endocrine Functions, pp. 191–209. New York: Plenum Press, 1976). At the 10 mg dose, 5-DIOL produced greater effects and completely reversed the potent stimulatory effect of ovariectomy to 0.86±0.17 ng/ml while the corresponding dose of DHEA only caused a 61% (p<0.01) inhibitory effect. However, at higher doses, DHEA and 5-DIOL were found to have similar effects, with the 30 mg and 100 mg dose, respectively, inhibiting serum LH levels by approximately 35% and 70% below the value found in intact control animals.

The effects on the circulating levels of the primary steroids and precursors produced by the administration of 5-DIOL and DHEA are shown in FIGS. 3 through 7. In particular, as shown in FIG. 3, treatment with DHEA causes serum DHEA to increase from undetectable levels in control ovariectomized animals to 1.74±0.30 nM ($p<0.01$), 3.67±0.59 nM ($p<0.01$), 12.9±3.69 nM ($p<0.01$) and 39.2±6.5 mM ($p<0.01$) after administration of the 3, 10, 30 and 100 mg dosages, respectively. On the other hand, a relatively constant but low level of serum DHEA was produced with the same dosages of 5-DIOL.

FIG. 4 shows the serum levels of 5-DIOL which are produced after administration with 5-DIOL and DHEA. While at the lower dose, 1 and 3 mg, 5-DIOL produced higher levels of 5-DIOL, at the higher doses, there was no significant difference in the levels of 5-DIOL produced by 5-DIOL and DHEA.

Figure 5:
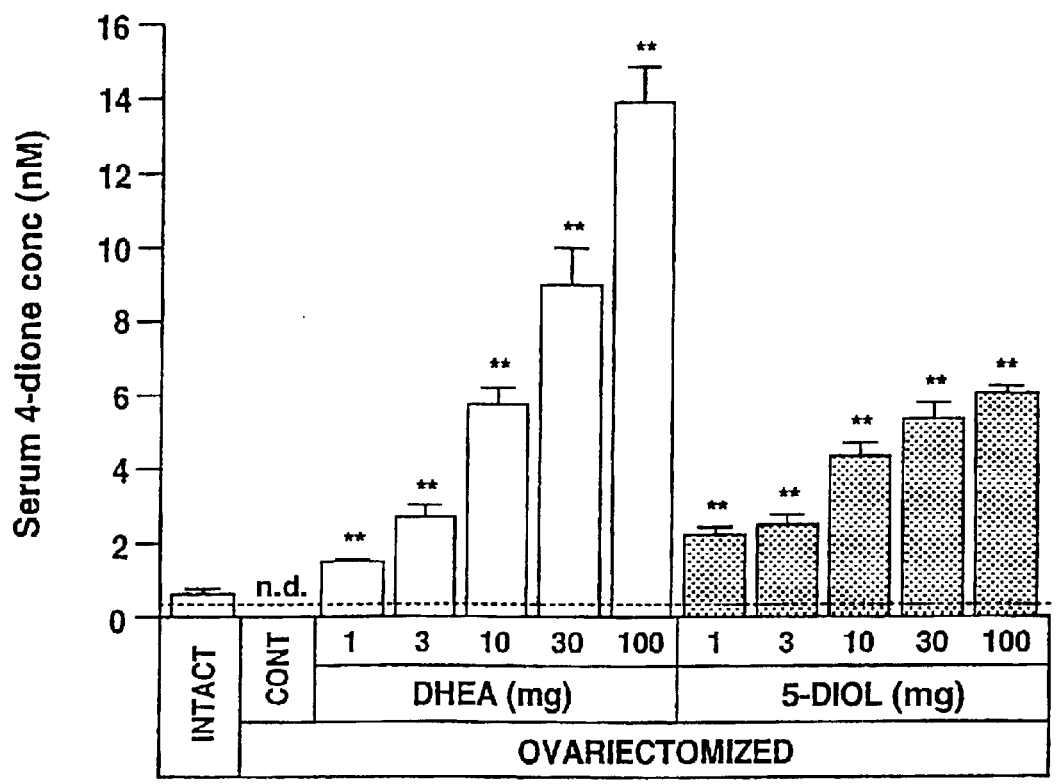
FIG. 5 is a graph of the effect of increasing doses of DHEA or 5-DIOL, administered percutaneously twice daily for 7 days, on the serum androstenedione (4-dione) concentration in ovariectomized rats, a measure of androgenic and/or estrogenic effect. Intact animals are used as additional controls. The compounds were dissolved in 50% ethanol–50% propylene glycol and were administered in 0.1 ml on the dorsal skin area (2 cm×2 cm).
Figure 6:
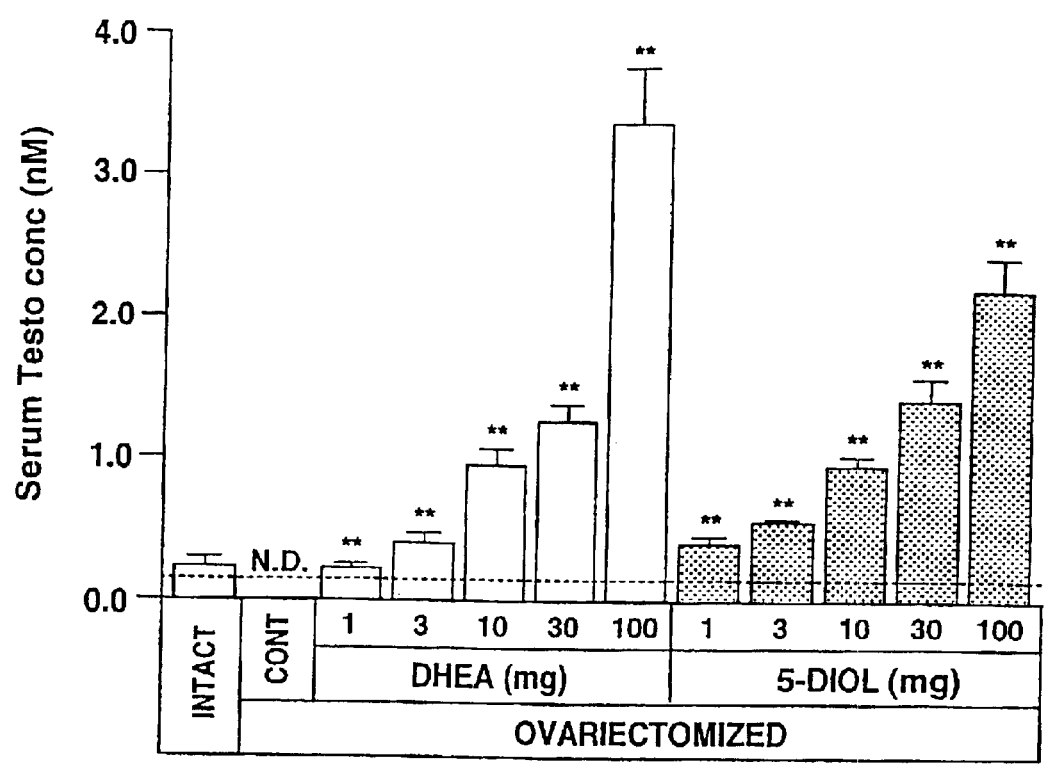
FIG. 6 is a graph of the effect of increasing doses of DHEA or 5-DIOL, administered percutaneously twice daily for 7 days, on the serum testosterone concentration in ovariectomized rats. Intact animals are used as additional controls. The compounds were dissolved in 50% ethanol–50% propylene glycol and were administered in 0.1 ml on the dorsal skin area (2 cm×2 cm).
Figure 7:
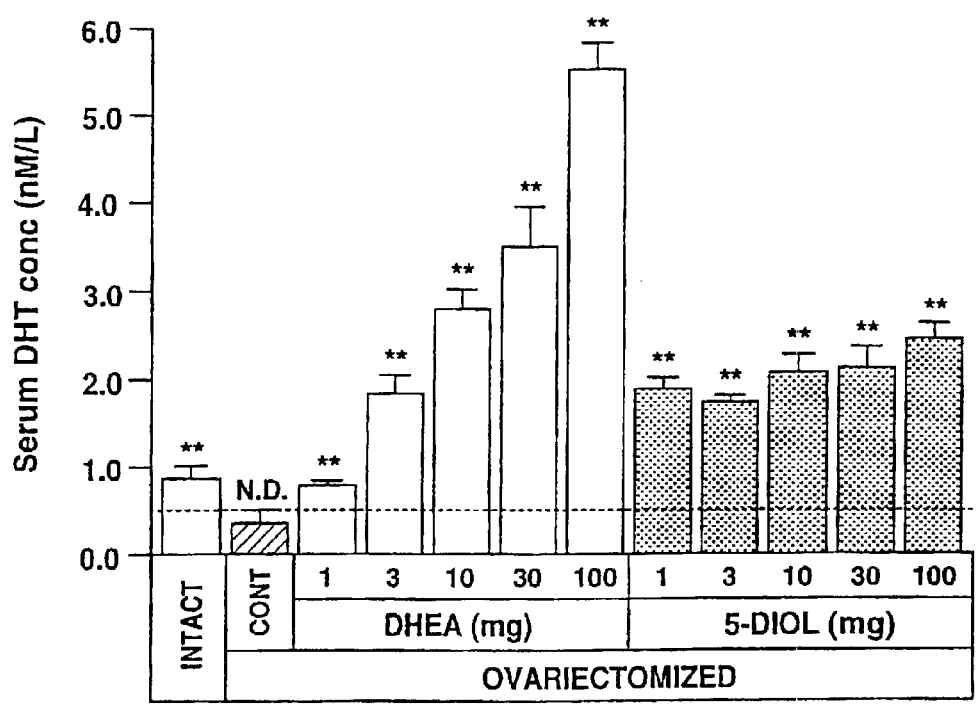
FIG. 7 is a graph of the effect of increasing doses of DHEA or 5-DIOL, administered percutaneously twice daily for 7 days, on the serum dihydrotestosterone (DHT) concentration in ovariectomized rats. Intact animals are used as additional controls. The compounds were dissolved in 50% ethanol–50% propylene glycol and were administered in 0.1 ml on the dorsal skin area (2 cm×2 cm).

The serum concentrations of 4-dione, testosterone and dihydrotestosterone (DHT) produced after administration of DHEA and 5-DIOL are shown in FIGS. 5 through 7. The levels of serum 4-dione, an androgenic indicator, produced by DHEA, ranged, depending on the dosage, from 30% to 125% higher than produced by 5-DIOL.

Consistent results were obtained with serum DHT and testosterone, both indicators of androgenic activity. Specifically, DHEA produced 30% to 125% higher serum DHT levels than 5-DIOL and at the highest dose, DHEA produced a 53% greater stimulatory effect on testosterone than the same dose of 5-DIOL. Furthermore, the levels of serum DHT produced by 5-DIOL remained substantially constant and relatively low across the dosage range.

Figure 8:
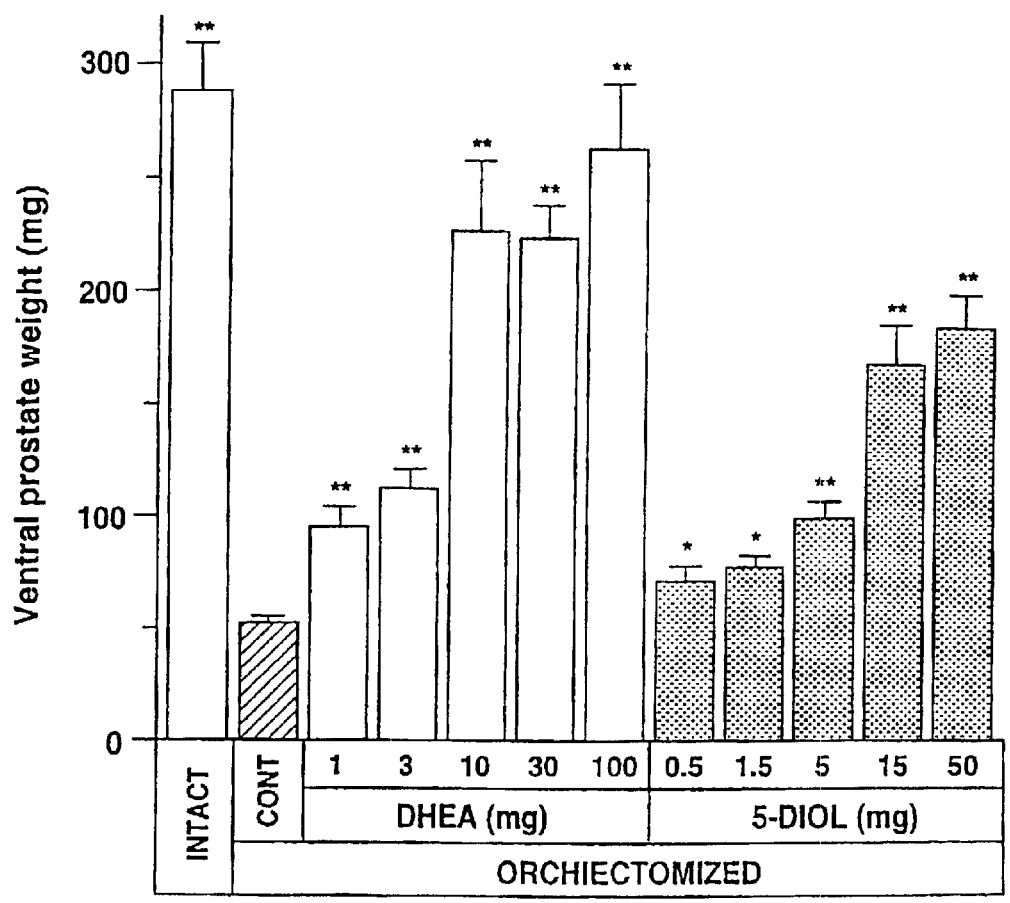
FIG. 8 is a graph of the effect of increasing doses of DHEA or 5-DIOL, administered percutaneously twice daily for 7 days, on the ventral prostate weight in orchiectomized rats, a measure of androgenic effect. Intact animals are used as additional controls.
Figure 9:
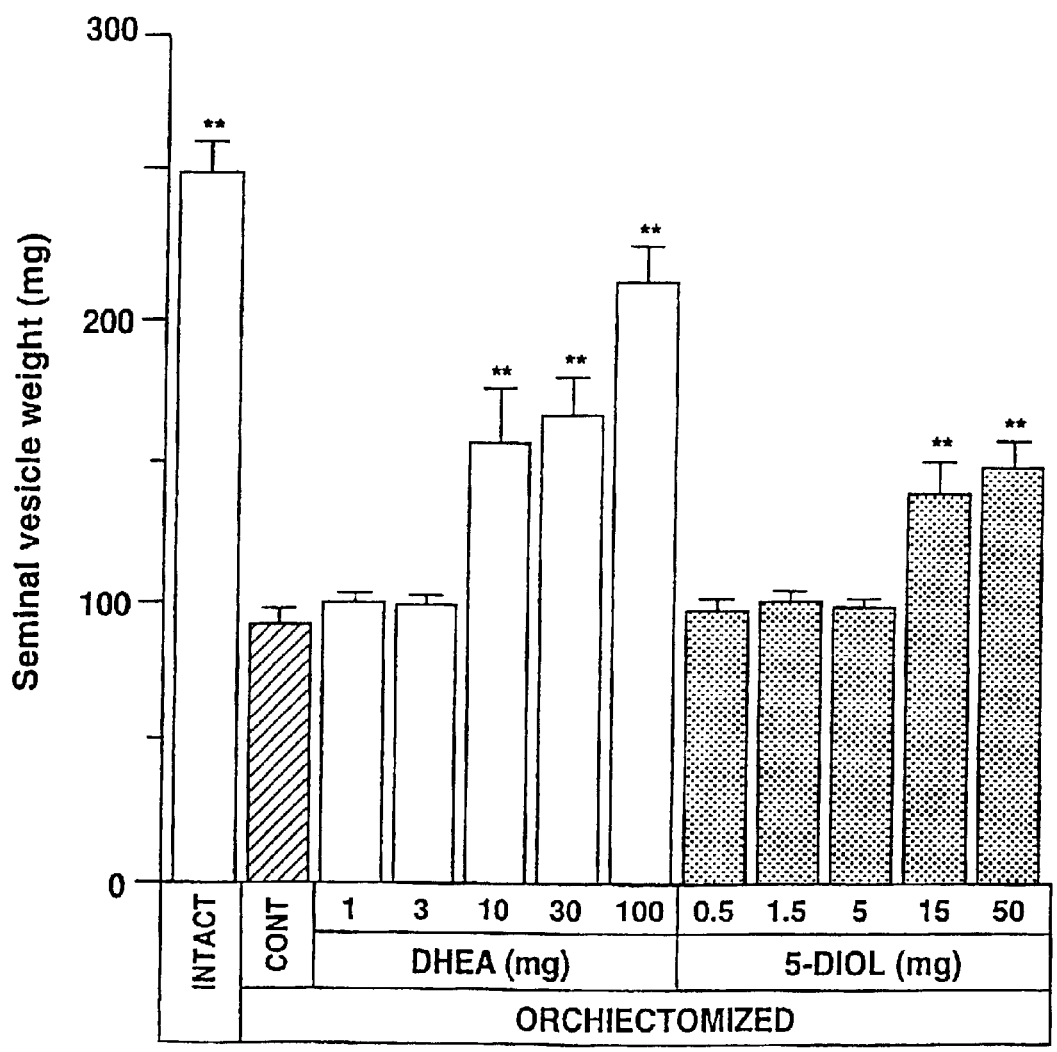
FIG. 9 is a graph of the effect of increasing doses of DHEA or 5-DIOL, administered percutaneously twice daily for 7 days, on the seminal vesicle weight in orchiectomized rats, a measure of androgenic effect. Intact animals are used as additional controls.

FIGS. 8 through 11 are directed to the effects of DHEA and 5-DIOL on a variety of well-recognized androgen-sensitive parameters in the orchiectomized rat. FIG. 8 shows the effects on ventral prostate weight, wherein at the 10 mg dose, DHEA was able to reverse by about 75% the inhibitory effect of orchiectomy while a 150% higher dose (15 mg) of 5-DIOL was only able to produce a 50% reversal of the effect of castration. In addition, DEHA was 1-fold more potent in increasing seminal vesicle weight, as shown in FIG. 9.

Furthermore, as shown in FIGS. 10 and 11, DHEA produced two to five times the effect produced by 5-DIOL on the concentration of the mRNAs encoding the C1 and C3 components of prostate binding protein (PBP) which, as discussed above, are precise indicators of androgenic activity. Moreover, the maximal levels of C1 and C3 PBP mRNAs achieved with the highest doses of 5-DIOL were only 17% to 37% of the levels obtained by DHEA.

Figure 12:
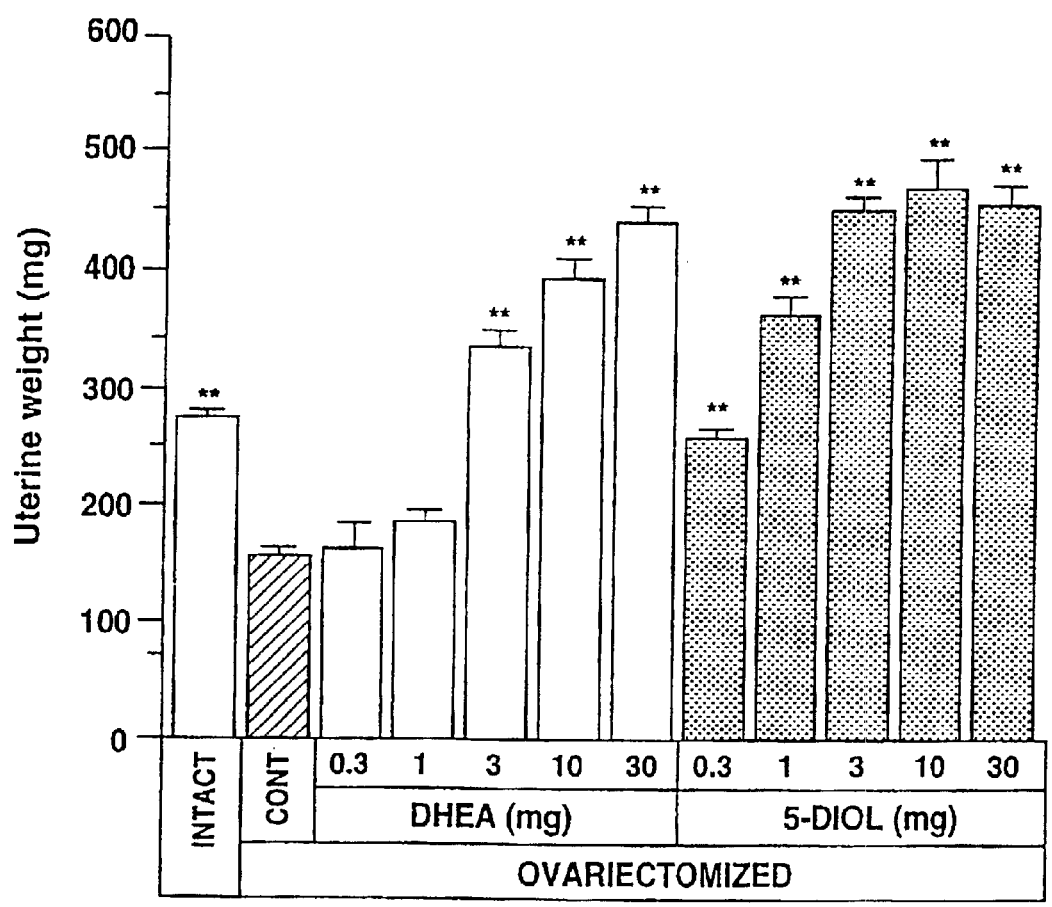
FIG. 12 is a graph of the effect of increasing doses of DHEA or 5-DIOL, administered subcutaneously twice daily for 7 days, on the uterine weight in ovariectomized rats, a measure of estrogenic effect. Intact animals are used as additional controls.
Figure 13:
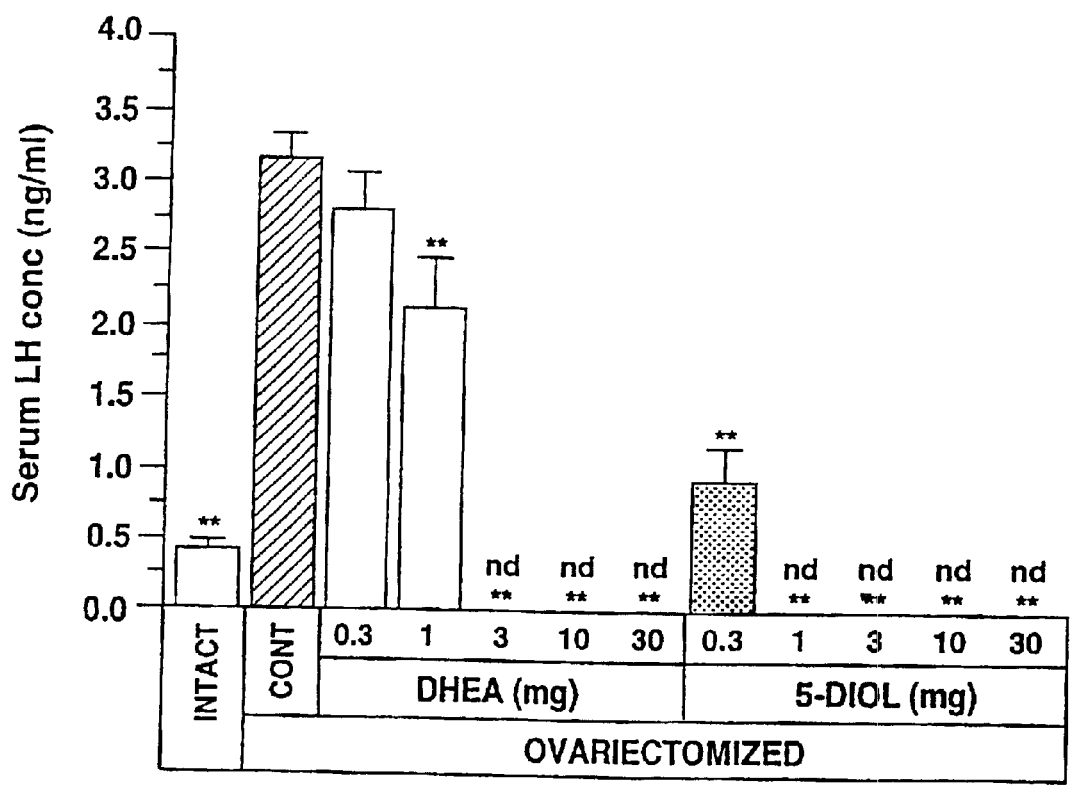
FIG. 13 is a graph of the effect of increasing doses of DHEA or 5-DIOL, administered subcutaneously twice daily for 7 days, on the serum LH concentration in ovariectomized rats, a measure of androgenic and/or estrogenic effect. Intact animals are used as additional controls.

FIGS. 12 through 16 show the effects of subcutaneous administration of DHEA and 5-DIOL on selected parameters described above. Since the two steroids were injected subcutaneously, these results provide a more direct measure of the relative estrogenic and androgenic activities of DHEA and 5-DIOL under conditions of optimal bioavailability. In particular, as shown in FIG. 12, 5-DIOL, at the lowest dose used, namely 0.3 mg, reversed by 90% the effect of 1-week ovariectomy on uterine weight (an estrogen-sensitive parameter) while DHEA, at the same dose, had no significant effect. However, at the higher dosages, the maximal stimulatory effect achieved by the two steroids was similar with a 2.8 to 2.9-fold stimulation. Furthermore, as calculated from the doses giving half-maximal stimulation of uterine weight (~2.5 mg for DHEA and 0.5 mg for 5-DIOL), 5-DIOL is approximately 5.0 times more uterotrophic than DHEA following subcutaneous administration. In addition, as shown in FIG. 13, 5-DIOL was found to be 5- to 7-fold more potent than DHEA in inhibiting the elevated serum LH levels indicated by castration.

Figure 16:
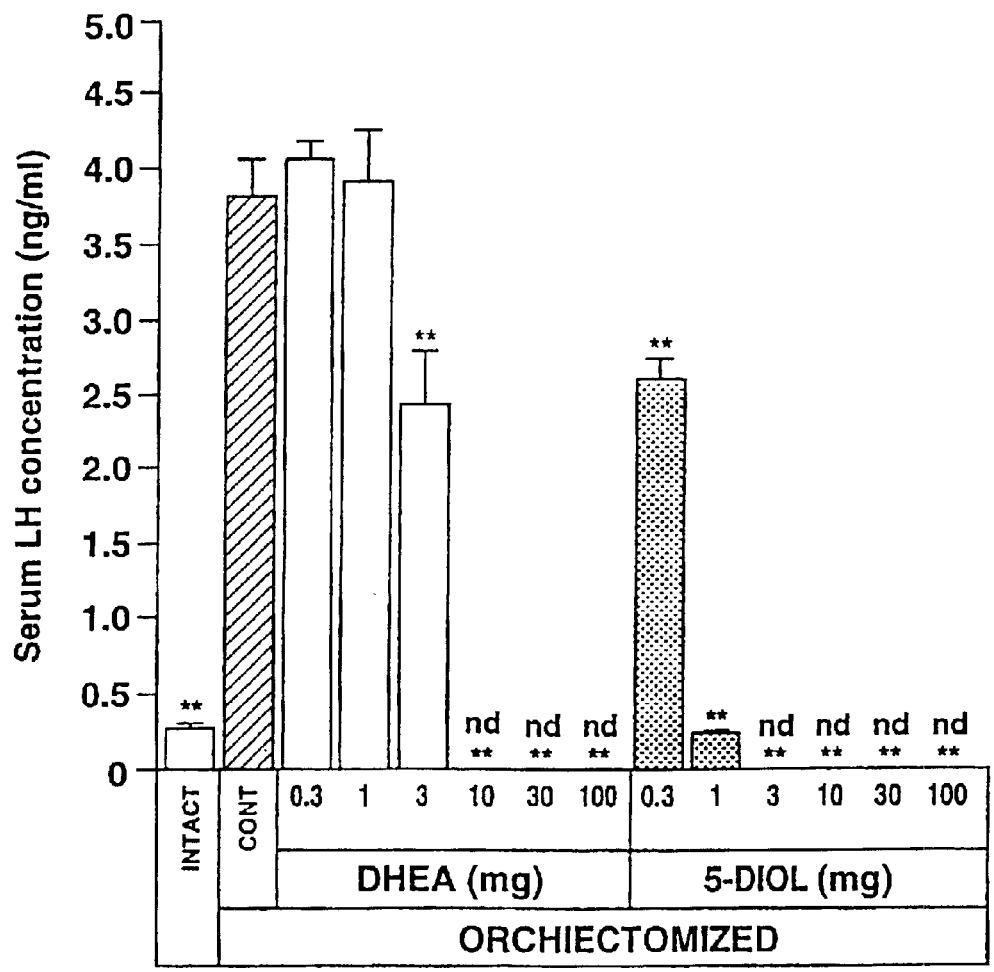
FIG. 16 is a graph of the effect of increasing doses of DHEA or 5-DIOL, administered subcutaneously twice daily for 7 days, on the serum LH concentration in orchiectomized rats, a measure of androgenic and/or estrogenic effect. Intact animals are used as additional controls.

As shown in FIG. 14, the maximal stimulatory effects on prostate and seminal vesicle weights (androgen-sensitive parameters; obtained with 5-DIOL were about 70% of the values achieved with DHEA. However, as calculated from the doses giving half-maximal reversal of the effect of orchiectomy ($ED_{50}$), DHEA and 5-DIOL had approximately an equal potency (i.e. an $ED_{50}$ value of 1 mg). On the other hand, the $ED_{50}$ values of maximal DHEA and 5-DIOL effects were calculated at 2.5 mg and 1.2 mg, respectively, for an estimated 2-fold higher potency of 5-DIOL compared to DHEA. Similarly, as shown in FIG. 15, for seminal vesicle weight, the maximal stimulatory effect of 5-DIOL was approximately 70% that of DHEA with half-maximal reversals of the effect of orchiectomy estimated at 2.5 and 1.2 mg, respectively, for DHEA and 5-DIOL for an estimated 2-fold high potency of 5-DIOL. On the prostatic concentrations of C1 and C3 PBP mRNAs, 5-DIOL was about twice as potent as DHEA. FIG. 16 shows the effects on serum LH concentration, with 5-DIOL being approximately 10 times more potent than DHEA.

From the foregoing, it may be seen that, at every concentration, the ratio of estrogenic to androgenic effects provided by DHEA is more heavily weighted toward androgenic effects than is that ratio for 5-DIOL.

Although the present invention has been described in relation to particular embodiments thereof, many other variations and modifications and other uses will be apparent to those skilled in the art.

What is claimed is:

1. A method for treating vaginal atrophy, comprising the step of administering a therapeutically effective amount of androst-5-ene-3β, 17β-diol or a prodrug thereof to a patient in need thereof.

2. The method of claim 1, wherein androst-5-ene-3β, 17β-diol is administered.

* * * * *